(12) United States Patent
Gunasekaran et al.

(10) Patent No.: US 11,567,051 B2
(45) Date of Patent: *Jan. 31, 2023

(54) NANOREACTORS AS THERMAL HISTORY INDICATORS

(71) Applicant: Wisconsin Alumni Research Foundation, Madison, WI (US)

(72) Inventors: Sundaram Gunasekaran, Madison, WI (US); Yi-Cheng Wang, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 139 days.

This patent is subject to a terminal disclaimer.

(21) Appl. No.: 16/807,759

(22) Filed: Mar. 3, 2020

(65) Prior Publication Data
US 2020/0278335 A1 Sep. 3, 2020

Related U.S. Application Data

(63) Continuation of application No. 15/176,550, filed on Jun. 8, 2016, now Pat. No. 10,578,598.

(60) Provisional application No. 62/318,923, filed on Apr. 6, 2016, provisional application No. 62/172,604, filed on Jun. 8, 2015.

(51) Int. Cl.
| | | |
|---|---|---|
| *G01N 33/02* | (2006.01) | |
| *B82Y 30/00* | (2011.01) | |
| *B82Y 40/00* | (2011.01) | |

(52) U.S. Cl.
CPC ............ *G01N 33/02* (2013.01); *B82Y 30/00* (2013.01); *B82Y 40/00* (2013.01)

(58) Field of Classification Search
CPC ........ G01N 33/02; G01N 33/00; B82Y 30/00; B82Y 40/00
USPC ...................................................... 436/147
See application file for complete search history.

(56) References Cited

U.S. PATENT DOCUMENTS

| | | |
|---|---|---|
| 5,085,802 A | 2/1992 | Jalinski |
| 6,544,925 B1 | 4/2003 | Prusik |
| 10,578,598 B2 * | 3/2020 | Gunasekaran ......... B82Y 30/00 |
| 2010/0172997 A1 | 7/2010 | Omary |
| 2018/0172598 A1 | 6/2018 | Gunasekaran |

OTHER PUBLICATIONS

Bagci, et al., A Simple and Green Route for Room-Temperature Synthesis of Gold Nanoparticles and Selective Colorimetric Detection of Cysteine, J. Food Sci. 2015, 80:9 N2071-8.
Brayner, R. et al., Preparation and characterization of metal (Au)— and bimetallic alloys (AuNi)—gelatin nanocomposites, Colloids and Surfaces A: Physicochem. Eng. Aspects 2005, 256:191-197.
Daniel, M.-C. et al., Gold nanoparticles: Assembly, supramolecular chemistry, quantum-size-related properties, and applications toward biology, catalysis, and nanotechnology, Chem. Rev. 2004, 104:293-346.
Finney, E. et al., Nanocluster nucleation and growth kinetic and mechanistic studies: A review emphasizing transition-metal nanoclusters, Journal of Colloid and Interface Science 2008, 317:351-374.
Frokjaer, S. et al., Protein drug stability: A formulation challenge, Nature Review Drug Discovery 2005, 4:298-306.
Ghosh, S. K. et al., Interparticle coupling effect on the surface plasmon resonance of gold nanoparticles: From theory to applications, Chem. Rev. 2007, 107:4797-4862.
Gunasekaran et al., A nanomaterial-based food thermal history indicator, (2011) Abstract, IFT Annual Meeting.
Huang, H. et al. "Synthesis of chitosan-stabilized gold nanoparticles in the absence/presence of tripolyphosphate." Biomacromolecules 5.6 (2004): 2340-2346.
Lim, S. et al., Gelatin-templated gold nanoparticles as novel time-temperature indicator. J Food Sci 2012, N45-N49.
Lu et al., Gelatin/gold nanoparticle-based thermal history indicator for food quality monitoring, (2013) Abstract No. 077-04, IFT Annual Meeting, New Orleans, LA, Jul. 13-16.
Neupane, et al., Synthesis of gelatin-capped gold nanoparticles with variable gelatin concentration, J Nanopart Res. 2010, 13 491-498.
Pal, T., Gelatin—A compound for all reasons, Journal of Chemical Education 1994, 71:679-681.
Patakfalvi, R. et al., The kinetics of homogeneous nucleation of silver nanoparticles stabilized by polymers, Journal of Nanoparticle Research 2007, 9:353-364.
Ray, P.C. Size and shape dependent second order nonlinear optical properties of nanomaterials and their application in biological and chemical sensing. Chem Rev 2010, 110:5332-5365.
Sardar, R. and Shumaker-Parry, J.S. Spectroscopic and microscopic investigation of gold nanoparticle formation: ligand and temperature effects on rate and particle size. J Am Chem Soc 2011, 133:8179-8190.
Shin, Y.,et al. "Preparation of homogeneous gold-silver alloy nanoparticles using the apoferritin cavity as a nanoreactor." The Journal of Physical Chemistry C 114.13 (2010): 5985-5989.
Sugimoto, T., "Formation of Monodispersed Nano- and Micro-Particles Controlled in Size, Shape, and Internal Structure," (2003) Cheml Eng Technol 26:313-321.
Wang et al., "Gold nanoparticle-based thermal history indicator for monitoring low-temperature storage," Microchim Acta (2015) published online (doi: 10.1007/s00604-015-1451-6).
Wang et al., "Green synthesis gold nanoparticle based visible thermal history indicator for food quality monitoring," (2015) Abstract, IFT Annual Meeting, Chicago, IL, July 11-14.

(Continued)

*Primary Examiner* — Christine T Mui
(74) *Attorney, Agent, or Firm* — Quarles & Brady, LLP

(57) ABSTRACT

Nanoreactors comprising a metal precursor in a carrier are provided as well as methods of initiating, methods of preparing, and methods of using nanoreactors. In some embodiments, upon exposure to heat, the metal precursor forms nanoparticles that can be detected, e.g., by detecting a color change in the nanoreactor and/or by detecting the number and/or size and/or size distribution and/or shape of the nanoparticles. The nanoreactors can be used, in some embodiments, as time-temperature indicators for perishable goods.

18 Claims, 39 Drawing Sheets

(56) References Cited

OTHER PUBLICATIONS

Wang, Y-C & Gunasekaran, S. Spectroscopic and microscopic investigation of gold nanoparticle nucleation and growth mechanisms using gelatin as a stabilizer. J Nanopart Res 2012, 14:1-11.
Yu, Y. et al., Gold nanorods: Electrochemical synthesis and optical properties, Journal of Physical Chemistry 1997, 101:6661-6664.
Zeisberg, M. et al., Biomarkers for epithelial-mesenchymal transitions, Journal of Clinical Investigation 2009, 119 (6):1429-1437.
Zhang, C. Time-Temperature indicator for perishable products based on kinetically programmable Ag overgrowth on Au nanorods. ACS Nano 2013, 7:4561-4568.
Zhang, J-J. et al., "Synthesis of Gelatin-Stabilized Gold Nanoparticles and Assembly of Carboxylic Single-Walled Carbon Nanotubes/Au Composites for Cytosensing and Drug Uptake," (2009) Anal. Chem. 81:16 6641-6648.
Office Action dated Oct. 21, 2014 in U.S. Appl. No. 13/209,947.
Office Action dated Dec. 30, 2015 in U.S. Appl. No. 13/209,947.
Office action dated Mar. 22, 2017 in U.S. Appl. No. 13/209,947.
Office Action dated May 4, 2015 in U.S. Appl. No. 13/209,947.
Office action dated Sep. 15, 2017 in U.S. Appl. No. 13/209,947.
Office Action dated Sep. 7, 2016 in U.S. Appl. No. 13/209,947.
U.S. Appl. No. 13/209,947, filed Aug. 15, 2011.
Office Action dated Jan. 29, 2020 in U.S. Appl. No. 15/844,256.

\* cited by examiner

The overall experimental design for gold nanoparticles (AuNPs) synthesis optimization and low-temperature storage tests conducted over 90 days with different durations at room temperature followed by frozen storage. The samples are designated as per Sample ID on the right.

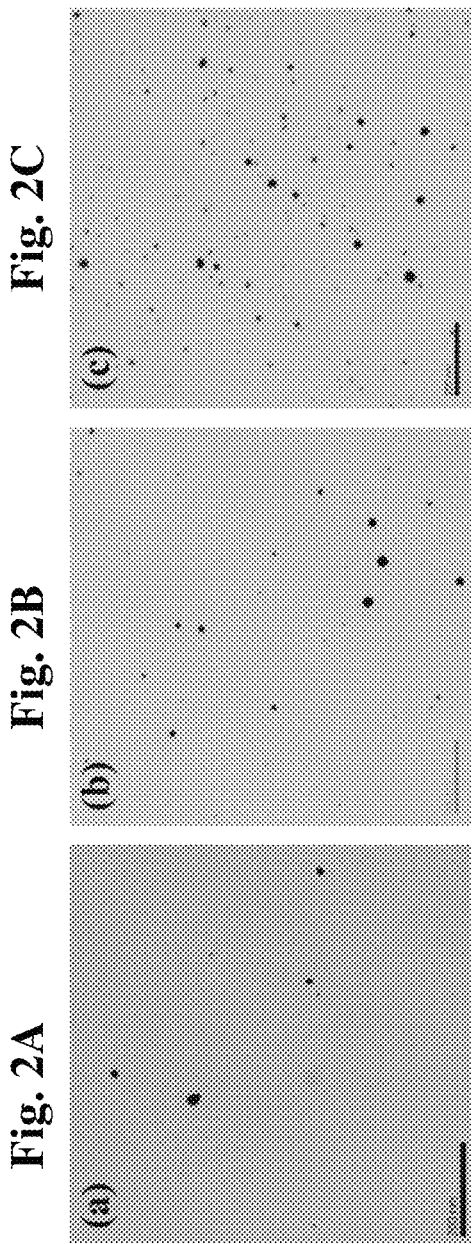
TEM images of AuNPs during the synthesis of THIs (0.1 v/v 10 mM of HAuCl₄ within 0.02 g·mL⁻¹ gelatin) after (a) 20, (b) 40, and (c) 60 min of heating at 90 °C.

TEM images of AuNPs during the synthesis of THIs (0.1 v/v 10 mM of HAuCl₄) with different gelatin concentrations (g mL⁻¹): (a) 0.01, (b) 0.02, and (c) 0.04 after 30 min of heating at 90 °C.

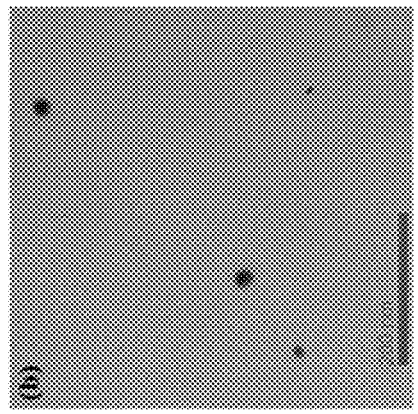

Fig. 4A

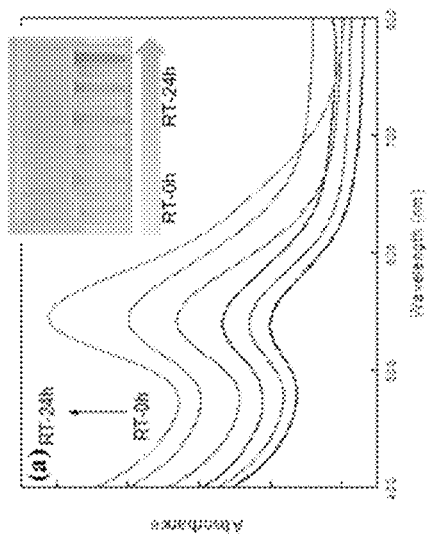

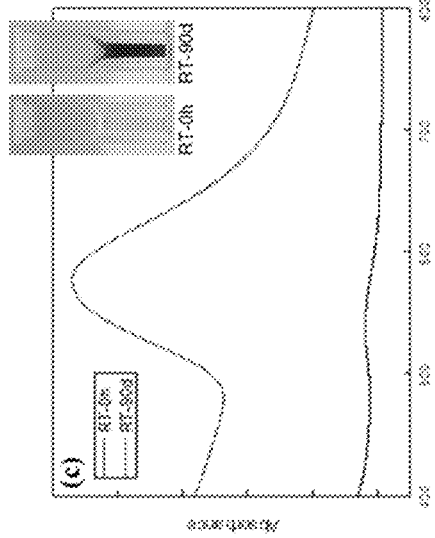

Fig. 4D a UV–vis spectra, and corresponding color (inset) of THs after storage at room temperature for 0 to 24 h followed by in a freezer at −20 °C for 90 days, b TEM image of an as-synthesized TH showing fairly spherical and small AuNPs, c UV–vis spectra and corresponding colors (inset) of the THs stored for 90 days at room temperature (RT-90d) and in a freezer at −20 °C (RT-0 h), d TEM image of the RT-90d sample showing large and polygonal-shaped AuNPs.

TEM images of the gold nanoparticles in THHs (0.1 v/v 10 mM of HAuCl₄+0.02 g·mL⁻¹ gelatin and heated at 90 °C for 10 min) after storage at room temperature for (a) 2 h and (b) 24 h followed by in a freezer at −20 °C for 90 days Illustration of AuNPs size and shape evolution in THs exposed to different storage times and temperatures. Generally, in our system, the size change is mainly due to storage temperature and the shape change due to storage time THs synthesized (using 0.1 v/v 10 mM of HAuCl4 with 0.02 g mL$^{-1}$ gelatin) at different temperatures: (a) 70, (b) 80, and (c) 90 °C. From left to right, sample color changed during heating at 4 min intervals from 8 to 60 min.

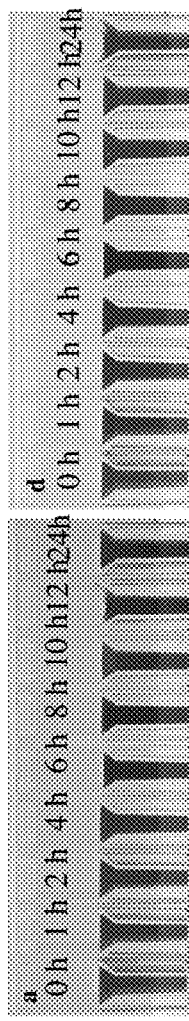
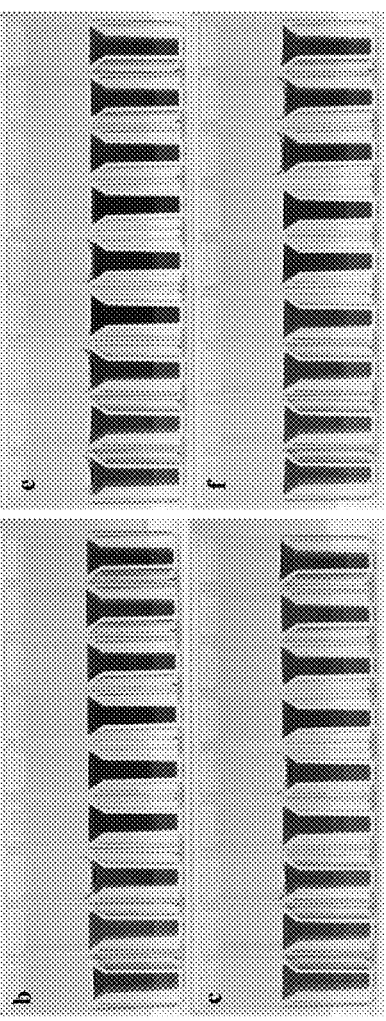
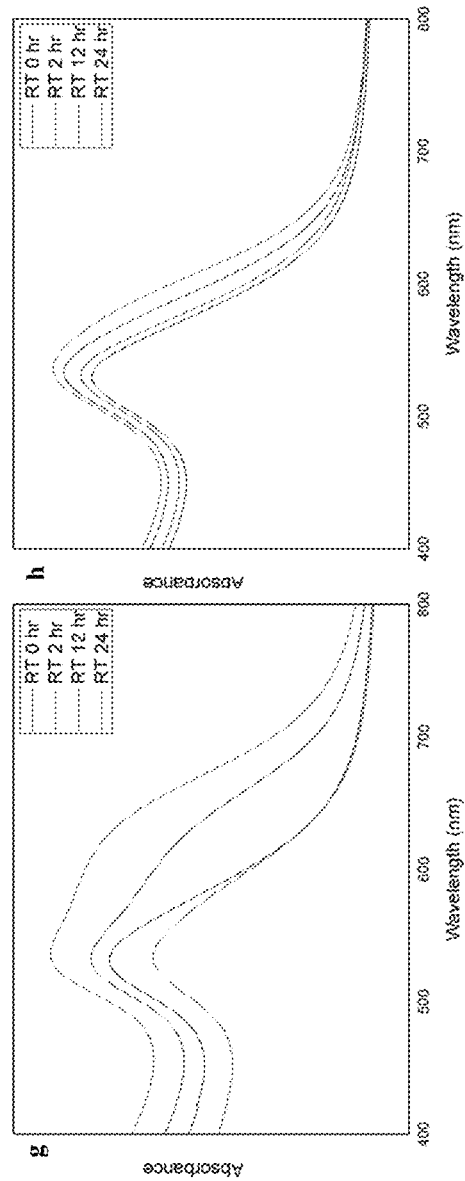
Fig. 13A  Fig. 13B  Fig. 13C  Fig. 13D  Fig. 13E  Fig. 13F  Fig. 13G  Fig. 13H

Figure 13I
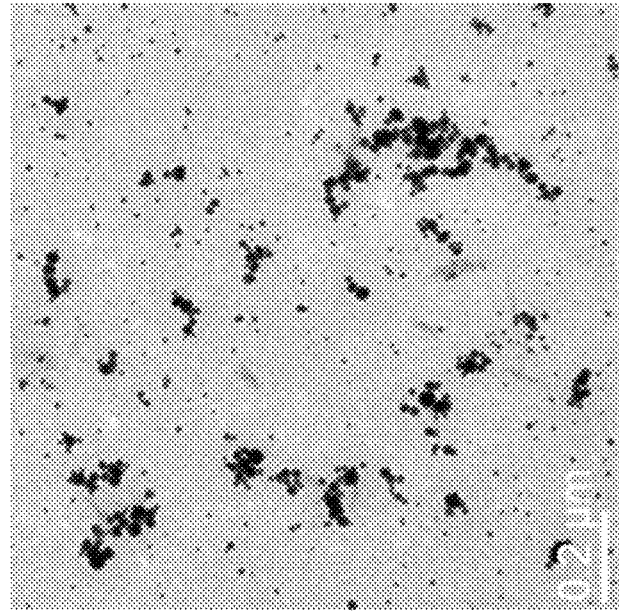
RT 24 h
Cont.
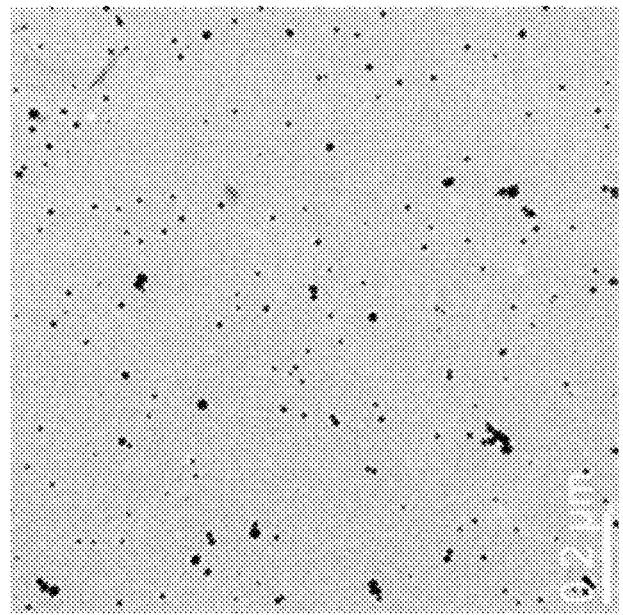
RT 0 h

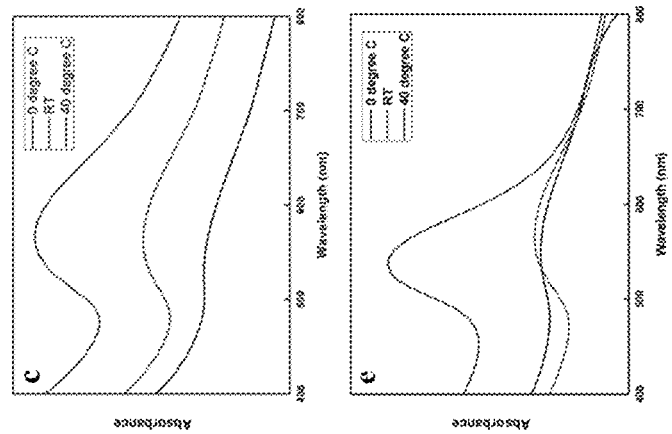
Fig. 14C
Fig. 14B
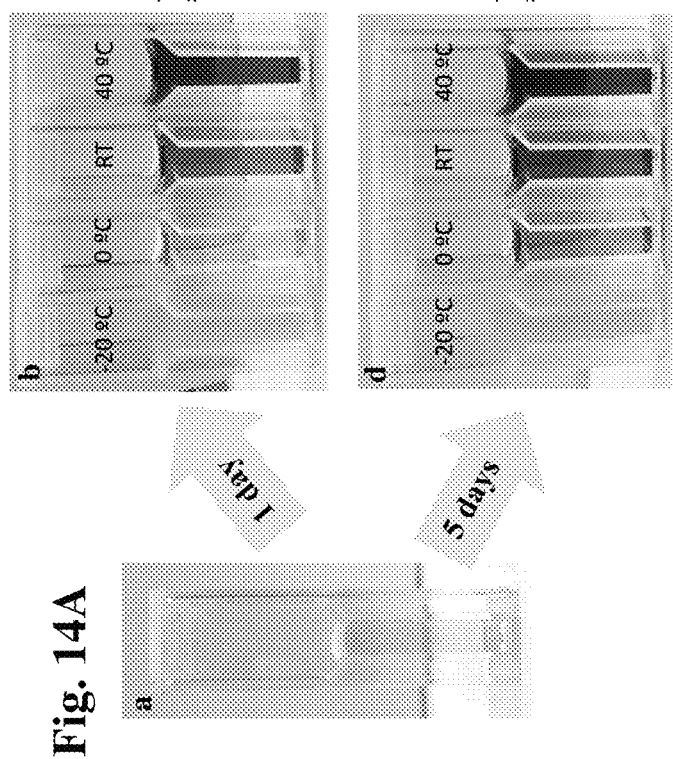
Fig. 14E
Fig. 14D
Fig. 14A
0.01 g · mL$^{-1}$ of Alginate; 1 mM HAuCl$_4$

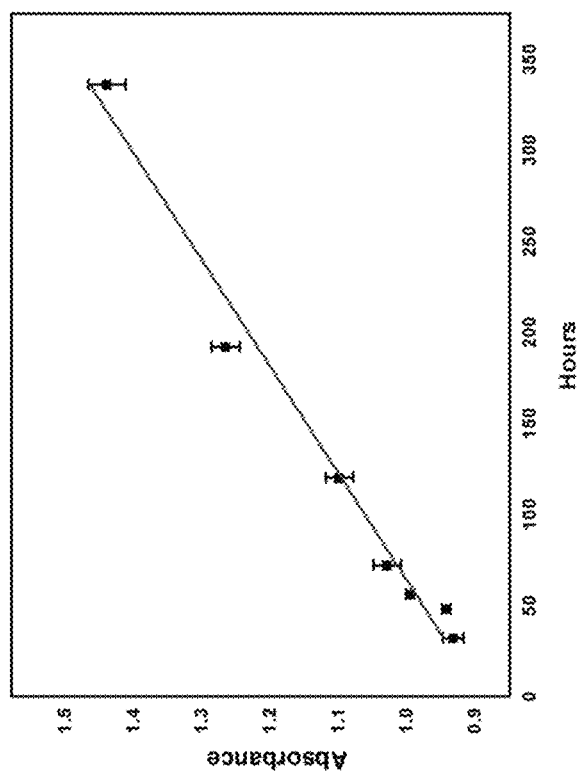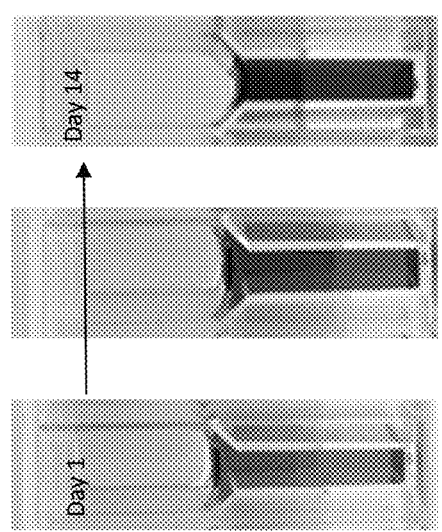
FIGURE 17

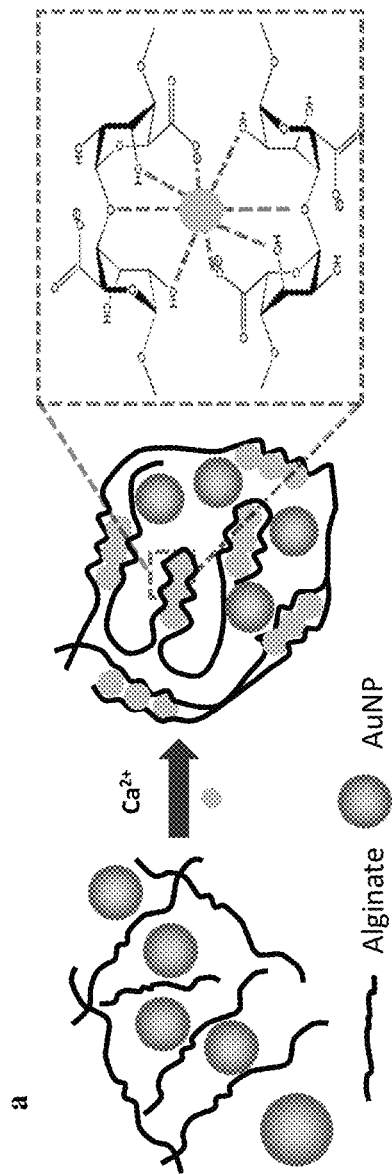
Fig. 18A
Fig. 18B
Fig. 18C

Figure 20. Color of the silver-gelatin nonreactor and corresponding UV-vis spectrum before (left) and after (right) HAuCl4 addition Figure 21. Color of the gold-silver-gelatin nonreactor and corresponding UV-vis spectrum 6 h after HAuCl4 addition

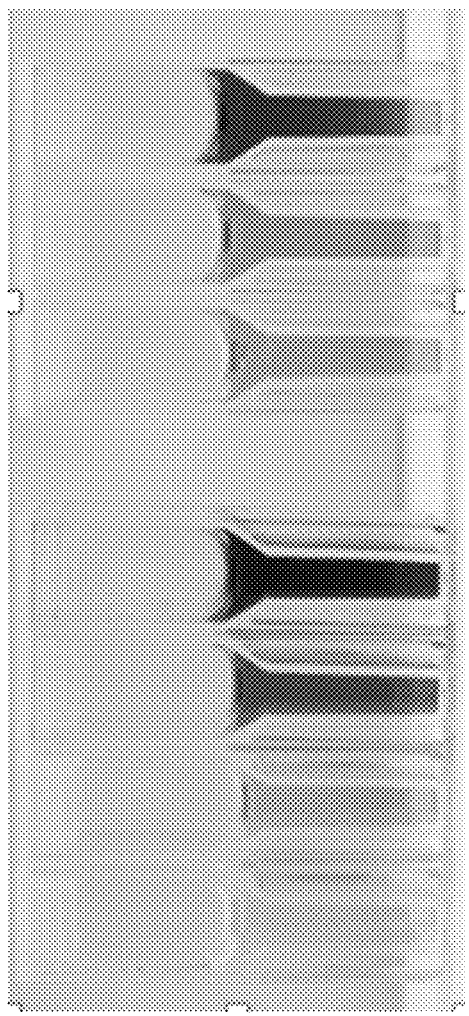

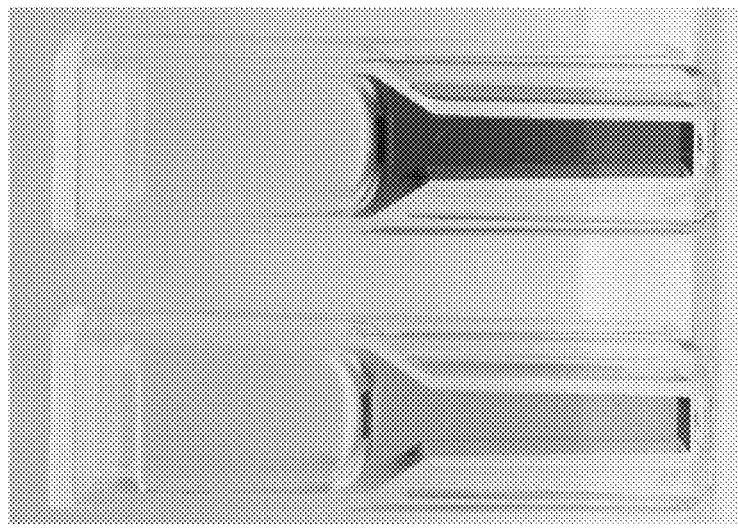
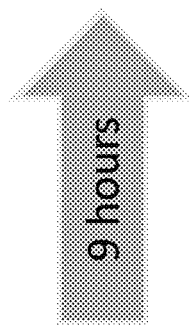
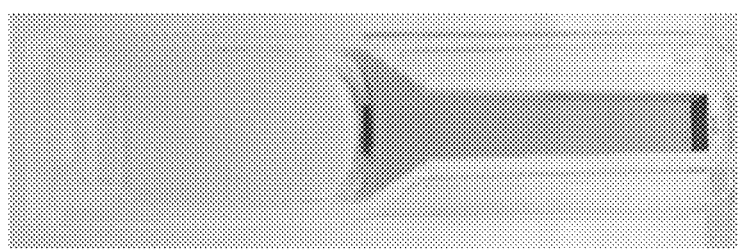
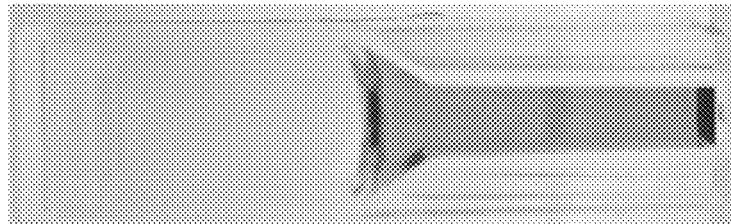
FIGURE 26

(mixture heated at 90 °C for 15 min)

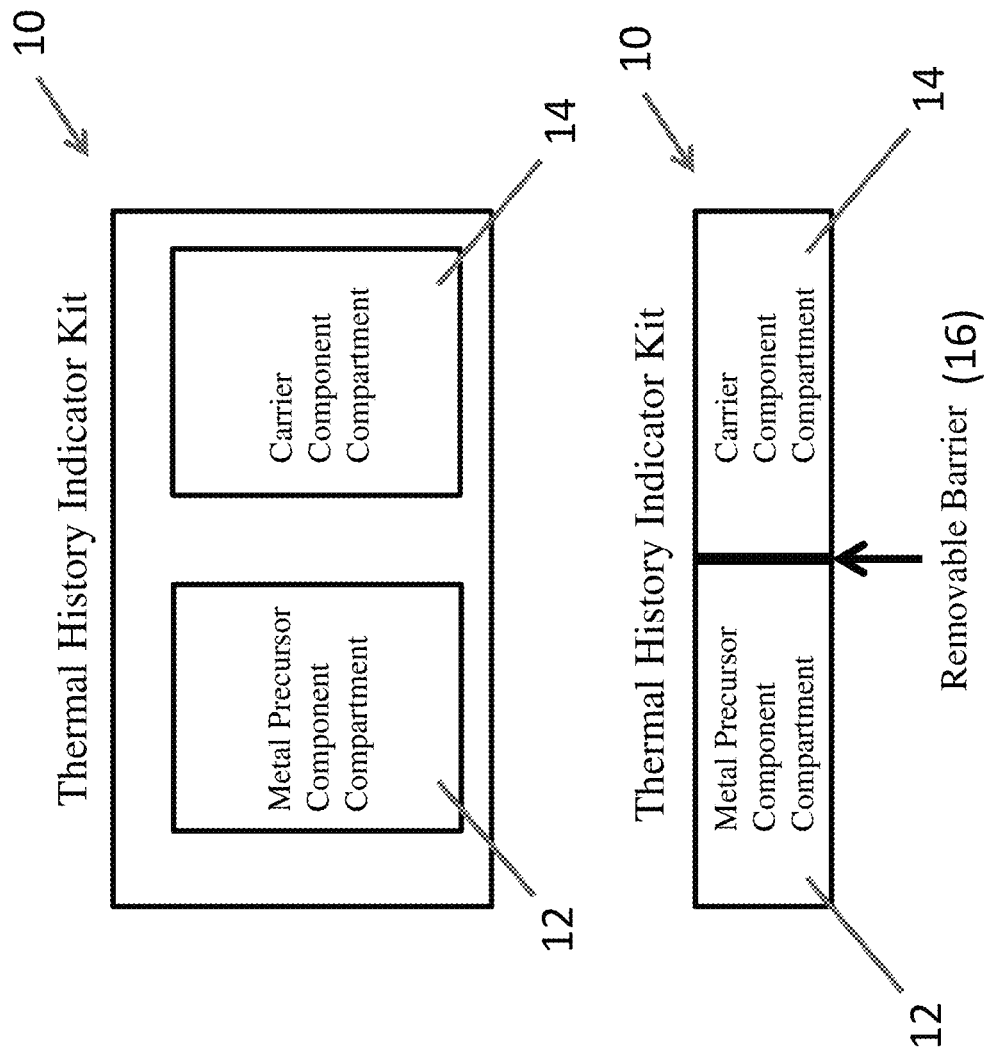

1hr 9 hr

NANOREACTORS AS THERMAL HISTORY INDICATORS

CROSS-REFERENCE TO RELATED APPLICATIONS

This patent application is a continuation of U.S. patent application Ser. No. 15/176,550, filed Jun. 8, 2016, which claims the benefit of priority of U.S. Provisional Patent Application No. 62/172,604, filed Jun. 8, 2015, and U.S. Provisional Patent Application No. 62/318,923, filed on Apr. 6, 2016, each of which are incorporated herein by reference in their entireties.

STATEMENT REGARDING FEDERALLY SPONSORED RESEARCH

This invention was made with government support under 14-CRHF-0-6055 awarded by the USDA/NIFA. The Government has certain rights in the invention.

INTRODUCTION

Many products used by consumers and businesses degrade with time. Such degradation may be due simply to aging or to environmental stress, e.g., in handling, transport, storage and in the hands of the consumer. Such products include food, pharmaceuticals, biologics, polymeric products, chemical products, and the like. Prematurely degraded products can pose health and safety risks to consumers, and monetary loss to businesses. Therefore, continual monitoring the quality of products is a persistent need to ensure their safety.

The need for quality monitoring of many kinds of materials and products has become increasingly important for both safety and economic reasons. Certain quality-degrading micro-environmental factors, such as gas composition and relative humidity, can be fairly well-controlled through packaging. Temperature, however, is an important factor affecting product quality that is often not adequately controlled during product distribution and storage. Thermal stress combined with time can cause spontaneous changes in materials or allow bacterial growth. Consequently, it is frequently beneficial to provide an indicator or sensor with a product to determine whether the product has been exposed to an undesirable thermal history and thus likely to have undergone substantial degradation or other undesired changes.

SUMMARY

Compositions, methods of initiating, methods of preparing, and methods of using nanoreactors as thermal history indicators are provided herein.

Nanoreactors may be comprised of at least one metal precursor and carrier. Exemplary biopolymers suitable for use as a carrier include gelatin, chitosan, and alginic acid. In some embodiments, the concentration of metal precursor is between 0.1 mM and 10 mM and the concentration of chitosan is between 0.0006 g/mL and 0.004 g/mL. In some embodiments, the concentration of metal precursor is between 0.1 mM and 10 mM and the concentration of alginic acid is between 0.001 g/mL and 0.1 g/mL.

In some embodiments, a nanoreactor comprises a first metal precursor, a second metal precursor and gelatin. The concentration of the first metal precursor may be between 0.01 mM and 100 mM, the concentration of the second metal precursor may be between 0.001 mM and 500 mM, and the concentration of the gelatin may be between 0.001 g/mL and 0.1 g/mL.

Methods of initiating a nanoreactor are also provided. The methods include mixing a nanoreactor solution comprising a first metal precursor and carrier with a precursor solution comprising a second metal precursor.

In some embodiments, nanoreactors are used as thermal history indicators comprising the nanoreactor in a container. In some embodiments, nanoreactors may be produced as thermal history indicator kits. A thermal history kit comprises a metal precursor component and a carrier component that are located in separate compartments in the kit. In some embodiments, the metal precursor component and the carrier component could be mixed so as to produce a nanoreactor.

In some embodiments, methods of preparing a nanoreactor are provided. The methods comprise preparing a nanoreactor, heating the nanoreactor to between 50° C. and 100° C. for between 30 seconds and 180 minutes, and cooling the nanoreactor to below −20° C., 0° C., 10° C., 15° C., or 25° C.

In some embodiments, methods of determining the thermal history of a nanoreactor are provided. Such methods comprise detecting at least one characteristic of the nanoreactor and based on said characteristic determining whether the nanoreactor was exposed to an undesired temperature for a time period. Such methods may be used to monitor a nanoreactor placed at a storage temperature for a time regime. In some embodiments, such methods may monitor a nanoreactor comprising gold precursor present at a concentration between 0.1 mM and 10 mM, gelatin present at a concentration between 0.01 g/mL and 0.04 g/mL, and water. The nanoreactor may be prepared by incubation at a temperature between 50° C. and 100° C. for between 0.5 and 180 minutes. The time regime may be more than 45 days or as little as 2 hours.

In some embodiments, methods of detecting exposure of a perishable good to an undesired temperature are provided. Such methods comprise exposing the perishable good, which is in association with a nanoreactor, to a storage temperature for a time regime, detecting at least one characteristic of the nanoreactor, and based on the characteristic determining whether the perishable good was exposed to an undesired temperature for a time period during storage.

BRIEF DESCRIPTION OF THE DRAWINGS

FIG. 2 shows Transmission Electron Microscopy (TEM) images of AuNPs during the synthesis of THIs (0.1 v/v 10 mM of $HAuCl_4$ within 0.02 $g \cdot mL^{-1}$ gelatin) after (FIG. 2A) 20 minutes, (FIG. 2B) 40 minutes, and (FIG. 2C) 60 min of heating at 90° C.

FIG. 3 shows TEM images of AuNPs during the synthesis of THIs (0.1 v/v 10 mM of $HAuCl_4$) with different gelatin concentrations ($g \cdot mL^{-1}$)

FIG. 4 shows THIs stored in a freezer and at room temperature. FIG. 4A shows UV-vis spectra, and corresponding color (inset) of THIs after storage at room temperature for 0 to 24 h followed by in a freezer at −20° C. for 90 days. FIG. 4B shows a TEM image of an as-synthesized THI showing fairly spherical and small AuNPs. FIG. 4C shows UV-vis spectra and corresponding color (inset) of the THIs stored for 90 days at room temperature (RT-90d) and in a freezer at −20° C. (RT-0h). FIG. 4D shows TEM image of the RT-90d sample showing large and polygonal-shaped AuNPs.

FIG. 7 also shows UV-Vis spectra of nanoreactors including 0.1 v/v 10 mM $HAuCl_{4+0.02}$ g/mL gelatin heated at 70, 80, and 90° C. for 60 min (FIG. 7D) and at 90° C. for 10 min to 60 min (FIG. 7E).

FIG. 8 shows color formation in a nanoreactor formed at room temperature. The nanoreactor on the left was comprised of 0.02 g·mL$^{-1}$ of gelatin with 1 mM $HAuCl_4$ and heated at 90° C. for 15 min before being placed at room temperature. The nanoreactor on the right was comprised of 0.02 g·mL$^{-1}$ of gelatin with 1 mM $HAuCl_4$ and placed at room temperature.

FIG. 9 shows photographs, TEM images, and UV-vis spectra of Chitosan-based nanoreactors with various concentrations of chitosan (0.0625%, 0.125%, and 0.25%) prepared using 1 mM of $HAuCl_4$ and heating at 90° C.

FIG. 11 shows the FTIR spectra and XPS spectra of chitosan/ and chitosan/AuNPs nanoreactors.

FIG. 13 shows temperature abuse studies using chitosan-based nanoreactors. The nanoreactors in FIGS. 13A and 13D were prepared as 0.2% of chitosan plus 1 mM of $HAuCl_4$ and heated at 90° C. for 15 min. The nanoreactors in FIGS. 13B and 13E were prepared as 0.25% of chitosan plus 1 mM of $HAuCl_4$ and heated at 90° C. for 15 min. The nanoreactors in FIGS. 13C and 13F were prepared as 0.3% of chitosan plus 1 mM of $HAuCl_4$ and heated at 90° C. for 15 min. The nanoreactors in FIGS. 13A-13C were then stored in −20° C. freezer for 2 days, then placed at RT for 0-24 hr, followed by returning to −20° C. for 1 additional day. The nanoreactors in FIGS. 13D-13F were stored in −20° C. freezer for 2 days, then placed at 40° C. for 0-24 hr, followed by returning to −20° C. for 1 additional day. FIGS. 13G and 13H show UV-vis spectra of nanoreactors shown in FIGS. 13B and 13C, respectively. All pictures and UV-vis spectra were obtained after thawing at RT for 2 hr and diluting 1:1 with DI water. FIG. 13I shows TEM images of 0.25 chitosan/AuNPs samples stored in −20° C. freezer for 2 days, then placed at RT for 0 h or 24 h before returning into freezer for additional 1 day. The 0.25 chitosan/AuNPs samples in FIG. 13I were prepared by mixing 0.25% chitosan with 1 mM of $HAuCl_4$ and heating at 90° C. for 15 min. As can be seen in FIG. 13I, the aggregation happened as RT exposure is increased.

FIG. 14 shows alginic acid-based nanoreactors. In FIG. 14A, an initial nanoreactor comprising 0.01 g·mL$^{-1}$ sodium alginate and 1 mM of $HAuCl_4$ was heated at 90° C. for 2.5 min. Portions of the initial nanoreactor were then placed at different temperatures (−20° C., 0° C., room temperature (RT), 40° C.) for two different periods of time (1 day or 5 days). FIG. 14B shows the color of the nanoreactors stored at −20° C., 0° C., room temperature (RT), or 40° C. after 1 day. FIG. 14D shows the color of the nanoreactors stored at −20° C., 0° C., room temperature (RT), or 40° C. after 5 days. FIG. 14C shows the absorbance spectrum of the nanoreactors in FIG. 14B. FIG. 14E shows the absorbance spectrum of the nanoreactors in FIG. 14D.

FIG. 15 shows the alginic acid-based nanoreactors described in FIG. 14 characterized by transmission electron microscopy (TEM). FIGS. 15C and 15D are higher magnification images of FIGS. 15A and 15B, respectively.

FIG. 16 shows results obtained using alginate nanoreactors.

FIG. 17 shows photographs of a nanoreactor including 0.01 g·mL$^{-1}$ of alginate plus 1 mM of $HAuCl_4$, which was heated at 90° C. for 2.5 minutes and then placed at RT for 1 to 14 days (Left). A plot of the UV-vis absorbance of the samples on the (Left) versus time is shown on the (Right).

FIG. 18 shows divalent ions can solidify alginic acid-based nanoreactors to form gel or solid systems. FIG. 18A shows how calcium ions can interact with the alginate biopolymer to form gels or solids. FIG. 18B shows a thermal history indicator hydrogel prepared by adding 100 μL of 1% calcium chloride solution into 1 mL of the as prepared alginate-$HAuCl_4$ solution mixture (0.01 g·mL$^{-1}$ sodium alginate and 1 mM of $HAuCl_4$ and heated at 90° C. for 2.5 min), which was stored at 0° C. for 2 h and exposure to room temperature (RT) for 0 (left) and 6 h (right) followed by storage at 0° C. for 24 h. FIG. 18C shows an alginic acid-based nanoreactor gel.

In FIG. 19A, three nanoreactors were synthesized by mixing 1 mM of hydrogen tetrachloroaurate ($HAuCl_4$) with 0.01 g/mL of alginic acid solution at 90° C. Each nanoreactor was then stored at −20° C. (freezer), 0° C. (fridge), or RT for 50 hours. The color of each nanoreactor (left) and UV-vis spectra (right) were then determined. In FIG. 19B, two nanoreactors were synthesized by mixing 1 mM of hydrogen tetrachloroaurate ($HAuCl_4$) with 0.01 g/mL of alginic acid solution at 90° C. Each sample was stored at 0° C. for 2 hours, placed at room temperature for 0 or 24 hours, and then placed back to 0° C. for one additional day before measurement. The color of each nanoreactor (left) and UV-vis spectra (right) were then determined. In FIG. 19C, two nanoreactors were synthesized by mixing 1 mM of hydrogen tetrachloroaurate ($HAuCl_4$) with 0.01 g/mL of alginic acid solution at 90° C. Each sample was stored at −20° C. for 2 hours, placed at room temperature for 0 or 24 hours, and then placed back to −20° C. for one additional day before measurement. The color of each nanoreactor (left) and UV-vis spectra (right) were then determined.

FIG. 24 shows nanoreactors including both silver and gold nanoparticles.

FIG. 25 shows that a multi-stage (starter switch) nanoreactor can be easily tunable for different applications. Nanoreactors in FIG. 25A were initially comprised of 0.01 $g·mL^{-1}$ of gelatin plus 1 mM $AgNO_3$. From left to right in FIG. 25A, 0.25 mM, 0.5 mM, 1 mM and 1.5 mM of $HAuCl_4$ were added and each nanoreactor was placed in a refrigerator for 3 days. Nanoreactors in FIG. 25B were initially comprised of 0.02 $g·mL^{-1}$ of gelatin plus 1 mM $AgNO_3$. From left to right in FIG. 25B, 0.5 mM, 1 mM and 1.5 mM of $HAuCl_4$ were added and each nanoreactor was placed in a refrigerator for 3 days.

FIG. 26 shows a multi-stage (starter switch) nanoreactor based on alginic acid. An initial nanoreactor comprising 0.01 $g·mL^{-1}$ of alginic acid plus 1 mM $AgNO_3$ was heated at 90° C. for 12 hours. At T=0, 0.5 mM of $HAuCl_4$ was added to the nanoreactor, which was stored for 9 hours at either 0° C. or room temperature.

FIG. 28 shows embodiments of a thermal history indicator kit. FIG. 28A shows one exemplary embodiment of a thermal history indicator kit. FIG. 28B shows another exemplary embodiment of a thermal history indicator kit.

FIG. 29 shows embodiments of a thermal history indicator kit comprising two metal precursors.

FIG. 30 compares the silver nanoparticle/gelatin nanoreactor prior to and after adding gold nanoparticles.

FIG. 31 allows comparison of silver nanoparticle/gelatin nanoreactors before and after adding gold nanoparticles. FIGS. 31A and 31B show 1 hr at 0° C. and RT. FIGS. 31C and 31D show 9 hr at 0° C. and RT (All these silver nanoparticles were synthesized alone and then added into gelatin.). As the storage temperature increased, along with the storage duration, the color becomes deeper. It is also tunable by changing the amount of gold precursor, gelatin concentration, amount of silver nanoparticles.

DETAILED DESCRIPTION

Figure 1:
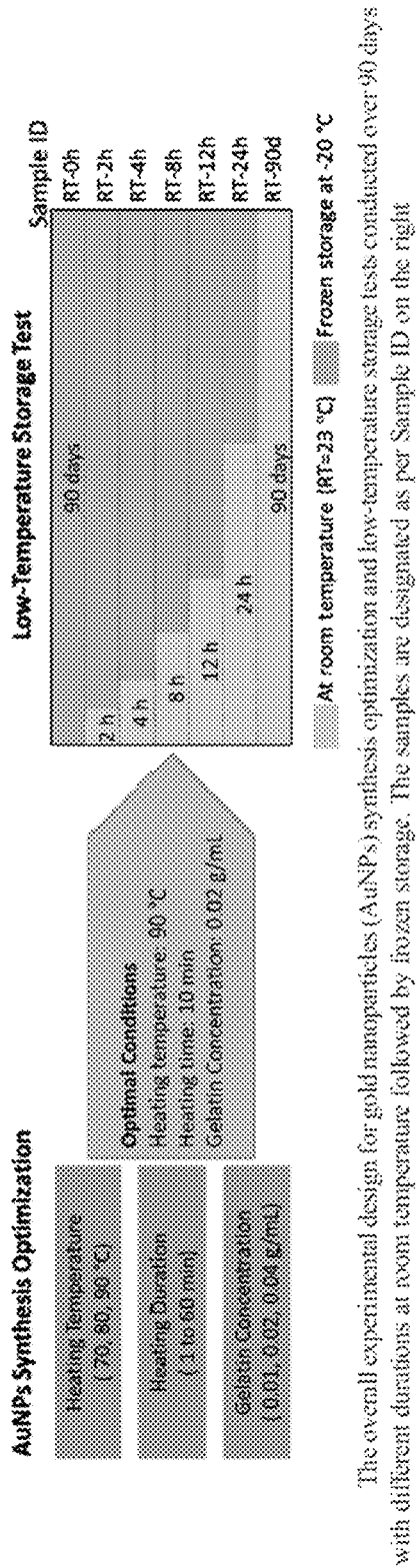
FIG. 1 shows experimental design for gold nanoparticles (AuNPs) synthesis optimization and low-temperature storage tests conducted over 90 days with different durations at room temperature followed by frozen storage. The samples are designated as per Sample ID on the right.

Metal nanoparticles, such as gold nanoparticles (AuNPs), have unique optical characteristics that can be used in the development of various sensors. Metal nanoparticle synthesis may occur in solutions comprising metal precursor salts, a reducing agent, and a capping agent. Metal nanoparticle synthesis occurs through a balance of nucleation, growth, and aggregation. Nanoreactor solutions in which metal nanoparticles may form have several characteristics that may be measured to indicate the conditions that the nanoreactors have experienced. Such characteristics include, but are not limited to, the color of the nanoreactor solution, the peak wavelength and peak absorption of the nanoreactor solution, the size, shape, and number of nanoparticles in the nanoreactor solution, and the size distribution of the nanoparticles in the nanoreactor solution. Generally, as shown in the Examples, the color of a nanoreactor solution will develop more slowly at lower temperatures and more quickly at higher temperatures.

Functional biopolymers (polyhydroxylated biomolecules such as proteins and polysaccharides) may be used as reducing/capping agents for 1-step nanoparticle synthesis. Exemplary biopolymers disclosed herein that may be used in nanoreactors include gelatin, chitosan, and alginic acid. Gelatin is an edible protein derived from collagen. Due to its low cost and ability to form a thermo-reversible hydrogel, gelatin is used in a myriad of practical applications. Further, gelatin is particularly well suited because it is both a reducing agent and a stabilizer. Accordingly, as gelatin is naturally oxidized, it reduces the metal precursor in the nanoreactor, inducing nanoparticle formation. Gelatin then serves to stabilize the nanoparticles once formed. In addition, the transparency of gelatin allows the visual detection of color changes in a nanoreactor.

Chitosan and alginic acid may also be used as reducing/capping agents for metal nanoparticle synthesis. Chitosan is a linear polysaccharide including β (1-4)-2-amino-2-deoxy-D-glucopyranose repeating units. Alginic acid is an anionic polysaccharide with homopolymeric blocks of (1-4)-linked β-D-mannuronate (M) and α-L-guluronate (G) residues, respectively, covalently linked together in different sequences or blocks. The monomers can appear in homopolymeric blocks of consecutive G-residues (G-blocks), consecutive M-residues (M-blocks) or alternating M and G-residues (MG-blocks).

Definitions

The term "metal precursor," as used herein, refers to a metal ion capable of nanoparticle formation under reducing conditions, whether or not the metal ion has been incorporated into a nanoparticle (i.e. reduced), is in solution, or otherwise. Concentrations of a metal precursor refer to the concentrations of the metal ion, whether or not the metal ion has been incorporated into a nanoparticle, is in solution, or otherwise. In some embodiments, a metal precursor is a metal ion capable of temperature-induced nanoparticle formation under reducing conditions. Nonlimiting exemplary metal precursors include gold ions, silver ions, platinum ions, palladium ions, copper ions, and nickel ions. In some embodiments, a metal precursor is a mixture of two or more metal ions. Nonlimiting exemplary metal precursors include AuNi, AuAg, AuAgCu, AuCu, AuPt, FeCoNi, NiCu, AgPd, FeCo, and PtIr. In some embodiments, a metal precursor is a "color-changing metal precursor," which refers to a metal precursor that is a first color, or no color, in solution, and which can form nanoparticles under certain reducing conditions, wherein the nanoparticles are a second color in solution after reduction. In some embodiments, the first color is no color (i.e., the metal precursor does not contribute to the color of the solution, so the solution may be clear). In some embodiments, the second color varies depending on the temperature at which the nanoparticles are formed. A nonlimiting exemplary color-changing metal precursor is gold precursor, gold-silver alloy (AuAg), and silver precursor.

The term "metal precursor salt," as used herein, refers to a salt of a metal precursor. A metal precursor salt may be a solid salt that can be dissolved in an appropriate solution. Once dissolved, the metal precursor salt separates into a metal ion and a counterion or counterions. Nonlimiting exemplary metal precursor salts include $HAuCl_4$, $KAuCl_4$, $NaAuCl_4$, and $AuCl_3$. In some embodiments, a metal precursor salt is a "color-changing metal precursor salt." Nonlimiting exemplary color-changing metal precursor salts include $HAuCl_4$, $KAuCl_4$, $NaAuCl_4$, and $AuCl_3$. Nonlimiting exemplary silver precursor salts include AgCl and $AgNO_3$.

The term "carrier," as used herein, refers to a polymer that is (a) capable of acting as a reducing agent, and (b) capable of stabilizing nanoparticles. In some embodiments, a carrier has a high capacity for holding soluble metal ions. In some embodiments, a carrier is capable of preventing or reducing aggregation of nanoparticles. In some embodiments, a carrier is capable of forming a gel. In some embodiments, a carrier comprises sulfur-containing substituents, such as thiols. In some embodiments, a carrier is a biopolymer. Nonlimiting exemplary biopolymers suitable for use as a carrier include gelatin, chitosan, and alginic acid.

The term "gelatin," as used herein, refers to a protein produced by denaturation of collagen, and derivatives of the protein produced by denaturation of collagen that retain the ability to (a) act as a reducing agent and (b) stabilize nanoparticles. Gelatin includes, but is not limited to, type A gelatin and type B gelatin. Gelatin may be derived from any suitable source of collagen, and from any suitable organism. Nonlimiting exemplary sources of gelatin include bovine, porcine, ovine, equine, and piscine.

The term "chitosan," as used herein, refers to a linear polysaccharide including β (1-4)-2-amino-2-deoxy-D-glucopyranose repeating units. Chitosan may be derived from any suitable source, and from any suitable organism. Nonlimiting exemplary sources of chitosan include shrimp head waste and shell, crab shell, squilla, squid pen, fungi, and insects.

The terms "alginic acid," as used herein, refers to is a polysaccharide including (1-4)-linked β-D-mannuronate (M) and α-L-guluronate (G) residues, respectively, covalently linked together in different sequences or blocks. Alginic acid may be derived from any suitable source, and from any suitable organism. Nonlimiting exemplary sources of alginic acid include brown algae and various seaweeds. As illustrated in the Examples, alginic acid may be used in the form of a salt. Exemplary alginic acid salts according to the present invention include, without limitation, alginic acid sodium salt or alginic acid potassium salt.

The term "nanoreactor," as used herein, refers to a composition comprising at least one metal precursor and a carrier.

The term "thermal history indicator" or "THI" or "THIs," as used herein, refers to a nanoreactor that is contained so as to keep the nanoreactor as one continuous mass. In some embodiments, a thermal history indicator is suitable for inclusion with, or in, a perishable good. In some embodiments, a thermal history indicator is contained in such a way that the presence of nanoparticles in the thermal history indicator can be detected without opening the system. In some embodiments, a thermal history indicator is encased in such a way as to facilitate the removal of a sample of the nanoreactor for detection of nanoparticles. The THI may be contained such that the color or other characteristics of the nanoreactor can be observed without opening the system. The THI may be contained in a container.

The term "container," as used herein, refers to any material capable of keeping a nanoreactor as one continuous mass. The container may be clear or translucent such that the color of the nanoreactor can be readily observed through the container. The container may be made of glass, plastic, metal, quartz, or any other suitable material.

The term "perishable good," as used herein, refers to an item or product that is negatively affected by elevated temperatures or if frozen. The term "negatively affected" means that the good becomes less suitable for the use for which it is intended. Nonlimiting exemplary ways in which a good may become less suitable include degradation, loss of potency, weakening, change in color, change in consistency, precipitation from solution, denaturation, risk of contamination and loss of viability. Exemplary perishable goods include, but are not limited to, food (including solid and liquid foods), pharmaceuticals, biologics, polymeric goods (such as rubbers, vinyls, polyesters, plastics, etc.), petroleum products (such as engine oil, etc.), fabrics (including linen, cotton, leather, etc.).

The term "perishable biologic," as used herein, refers to biologic goods that are negatively affected by elevated temperatures. Biologic goods include, but are not limited to, proteinaceous therapeutics, such as antibodies, proteins, and peptides; vaccines; blood and blood components; cells; tissues; organs; and clinical and medical samples, such as blood and blood components, cells, tissues, organs, biopsy tissue, bodily fluids, etc.

The term "undesired temperature," as used herein, refers to a temperature above or below the acceptable storage temperature of a perishable good. Thus, if the acceptable storage temperature of a perishable good is 4° C. to 10° C., an undesired temperature is a temperature above 10° C. or above 20° C. or a temperature below 0° C. or below −10° C. or −20° C. If the acceptable storage temperature of a perishable good is between 20° C. and 30° C., an undesired temperature is a temperature above 30° C. or below 0° C. If the acceptable storage temperature of a perishable good is less than 0° C., i.e. −20° C. or −80° C., an undesired temperature is a temperature above 0° C. or above 10° C. or even above 20° C.

Exemplary Nanoreactors

Nanoreactors are provided herein. A nanoreactor comprises a metal precursor and a carrier. In some embodiments, the metal precursor and carrier are dissolved in water.

In some embodiments, a nanoreactor comprises a metal precursor present in the nanoreactor at a concentration of between 0.1 mM and 10 mM, or between 0.2 mM and 3 mM, or between 0.5 mM and 2 mM, or between 0.5 mM and 1.5 mM, or about 1 mM. The carrier may be chitosan which is present in the nanoreactor at a concentration of between 0.0001 g/mL and 0.1 g/mL, or between 0.0006 g/mL and 0.004 g/mL, or between 0.001 g/mL and 0.0035 g/mL, or between 0.002 g/mL and 0.003 g/mL, or about 0.00125 g/mL, or about 0.0025 g/mL. In some embodiments, a nanoreactor comprises a metal precursor present in the nanoreactor at a concentration of between 0.2 mM and 3 mM, and chitosan which is present in the nanoreactor at a concentration of between 0.0006 g/mL and 0.004 g/mL and the reactor is prepared by incubation at a temperature between 70° C. and 95° C. for between 1 and 60 minutes and then cooled to a temperature between −100° C. and 10° C. for use as a THI. In some embodiments, a nanoreactor comprises a metal precursor present in the nanoreactor at a concentration of between 0.2 mM and 3 mM, and chitosan which is present in the nanoreactor at a concentration of between 0.0006 g/mL and 0.004 g/mL and the reactor is prepared by incubation at a temperature between 20° C. and 30° C. (Preferably room temperature) before use as a THI.

In some embodiments, the carrier is alginic acid which is present in the nanoreactor at a concentration of between 0.001 g/mL and 0.1 g/mL, or between 0.005 g/mL and 0.015 g/mL, or about 0.01 g/mL. In some embodiments, a nanoreactor comprises a metal precursor present in the nanoreactor at a concentration of between 0.2 mM and 3 mM, and alginic acid which is present in the nanoreactor at a concentration of between 0.001 g/mL and 0.1 g/mL. The reactor may be prepared by incubation at a temperature between 70° C. and 95° C. for between 1 and 60 minutes and then cooled to a temperature between −100° C. and 10° C. before use as a THI. In some embodiments, a nanoreactor comprises a metal precursor present in the nanoreactor at a concentration of between 0.2 mM and 3 mM, and alginic acid which is present in the nanoreactor at a concentration of between 0.001 g/mL and 0.1 g/mL and the reactor may be prepared by incubation at a temperature between 20° C. and 30° C. (Preferably room temperature) before use as a THI. Any of the alginic acid-based nanaoreactors described herein may further comprise a divalent ion including, without limitation, a calcium ion, a magnesium ion, a strontium ion, a barium ion, or any combination thereof. When combined with divalent ions, the alginic acid-based nanaoreactors described herein may form hydrogels.

In some embodiments, a nanoreactor comprises a first metal precursor, a second metal precursor, and a carrier, wherein the concentration of the first metal precursor is between 0.01 mM and 100 mM, the concentration of the second metal precursor is between 0.001 mM and 500 mM, and the concentration of the carrier is between 0.0005 g/mL and 0.1 g/mL. In some embodiments, the first metal precursor is gold precursor and the second metal precursor is silver precursor. In some embodiments, the first metal precursor is silver precursor and the second metal precursor is gold precursor. In some embodiments, the gold precursor is between 0.01 mM and 100 mM. In some embodiments, the carrier may be gelatin or alginic acid.

In some embodiments, a nanoreactor is prepared by incubation at a temperature between 70° C. and 95° C. for between 1 and 60 minutes and then cooled to a temperature between −100° C. and 25° C. In some embodiments, a nanoreactor may be prepared by incubation at a temperature between 20° C. and 30° C. (Preferably room temperature).

In some embodiments, the metal precursor is gold precursor. In some embodiments, gold precursor in the nanoreactor comes from dissolving a gold salt selected from $HAuCl_4$, $KAuCl_4$, $NaAuCl_4$, and $AuCl_3$ in the nanoreactor. In some embodiments, the metal precursor is a silver precursor. The silver in the nanoreactor may come from dissolving a silver salt selected from $AgCl$ and $AgNO_3$.

In some embodiments, a nanoreactor comprises a gold precursor present in the nanoreactor at a concentration of about 1 mM and chitosan present in the nanoreactor at a concentration of about 0.0025 g/mL. In some embodiments, a nanoreactor comprises a gold precursor present in the nanoreactor at a concentration of about 1 mM and chitosan present in the nanoreactor at a concentration of about 0.0025 g/mL and is prepared by incubation at 90° C. for 15 minutes and then cooled to a temperature of about −20° C. In some embodiments, a nanoreactor comprises a gold precursor present in the nanoreactor at a concentration of about 1 mM and chitosan present in the nanoreactor at a concentration of about 0.0025 g/mL and is prepared by incubation at a temperature between 20° C. and 30° C. (Preferably room temperature).

In some embodiments, a nanoreactor comprises a gold precursor present in the nanoreactor at a concentration of about 1 mM and alginic acid present in the nanoreactor at a concentration of about 0.01 g/mL. In some embodiments, a nanoreactor comprises a gold precursor present in the nanoreactor at a concentration of about 1 mM and alginic acid present in the nanoreactor at a concentration of about 0.01 g/mL and is prepared by incubation at 90° C. for 2.5-4.5 minutes and then cooled to a temperature of about 4° C. In some embodiments, a nanoreactor comprises a gold precursor present in the nanoreactor at a concentration of about 1 mM and alginic acid present in the nanoreactor at a concentration of about 0.01 g/mL and is prepared by incubation at a temperature between 20° C. and 30° C. (Preferably room temperature).

In some embodiments, a nanoreactor comprises a metal precursor, a first carrier, and a second carrier. The concentration of the metal precursor may be between 0.01 mM and 10 mM. The concentration of the first carrier may be between 0.001 g/mL and 0.1 g/mL and the concentration of the second carrier may be between 0.0005 g/mL and 0.1 g/mL. In some embodiments, the first carrier and the second carrier are gelatin and alginic acid, respectively.

Exemplary Methods for Initiating Nanoreactors

Methods of initiating nanoreactors are provided herein. Such methods comprise, in some embodiments, mixing a nanoreactor solution comprising a first metal precursor and carrier with a precursor solution comprising a second metal precursor to produce a final solution comprising the first metal precursor, the second metal precursor, and the carrier. The nanoreactor solution may be prepared by synthesizing nanoparticles with the first metal precursor using any suitable reducing reagent, including, without limitation, sodium borohydride and citrate and then mixing the solution with the carrier. Alternatively, the nanoreactor solution may be formed by synthesizing nanoparticles with the first metal precursor in situ by adding the carrier. In some embodiments, the precursor solution and nanoreactor solution further comprise water. In some embodiments, the concentration of the first metal precursor in the final solution is between 0.001 mM and 500 mM. In some embodiments, the concentration of said second metal precursor in the final solution is between 0.01 mM and 100 mM. In some embodiments, the concentration of the first metal precursor in the final solution is between 0.001 mM and 500 mM and the concentration of the second metal precursor in the final solution is between 0.01 mM and 100 mM, and the concentration of the carrier in the final solution is between 0.001 g/mL and 0.1 g/mL. In some embodiments, the first metal precursor is silver precursor, the second metal precursor is gold precursor, and the carrier is gelatin.

In some embodiments, the methods of initiating a nanoreactor may include preparing a nanoreactor solution comprising a first metal precursor and carrier; incubating the nanoreactor solution for a first period of time either in association with a perishable good or not; mixing the nanoreactor solution with a precursor solution comprising a second metal precursor to produce a final solution comprising the first metal precursor, the second metal precursor, and the carrier; and incubating the final solution for a second period of time either in association with a perishable good or not. The first and second periods of time may be for any period of time between 10 minutes to 6 months and not necessarily be the same period of time.

Exemplary Thermal History Indicators

Thermal History Indicators are provided herein. In some embodiments, a nanoreactor is part of a thermal history indicator. A thermal history indicator ("THI") comprises a nanoreactor in a container. A container refers to any material capable of keeping a nanoreactor as one continuous mass. Nonlimiting exemplary containers include, for example, materials made from glass, plastic, quartz, metal, micelles, liposomes, membranes, gels (such as agar), etc.

In some embodiments, a thermal history indicator is designed such that nanoparticles can be detected without opening the thermal history indicator, if the nanoparticles will be detected visually, e.g., by observing a color change, the thermal history indicator container will not interfere with the visual detection. In some such embodiments, the thermal history indicator container is translucent, for example, it is made from glass, clear plastic, or quartz. In some embodiments, the thermal history indicator container is clear (i.e., lacking detectable color). In some embodiments, the thermal history indicator container is colored, but translucent. In some such embodiments, the color of the thermal history indicator container does not interfere with the visual detection of the nanoparticles in the nanoreactor, or even enhances the visual detection.

In some embodiments, a thermal history indicator is designed such that nanoparticles can be detected in the nanoreactor through other means without opening the nanoreactor. For example, in some embodiments, the nanoparticles are detected using x-ray radiography. In some such embodiments, the thermal history indicator container does not interfere with detection by x-ray radiography. That is, in some such embodiments, the thermal history indicator container is not made of a material that blocks x-rays, such as lead.

In some embodiments, a thermal history indicator is designed such that a sample can be taken for detection of nanoparticles. In some such embodiments, the thermal history indicator container includes a portion that can be opened for collection of a sample. After opening, the thermal history indicator container can either be resealable or non-resealable. In some embodiments, a thermal history indicator includes a cartridge or other removable portion that contains at least a sample of the nanoreactor. In some embodiments, the cartridge or other removable portion is suitable for detecting nanoparticles in the nanoreactor by a selected method.

In some embodiments, a sample of the nanoreactor is removed from the thermal history indicator for detection by a selected method. Such removal may be by any suitable method, including pipetting, pouring, capillary action, etc. In some embodiments, a thermal history indicator includes a device for facilitating removal of a sample from the nanoreactor. Nonlimiting exemplary devices include pipets, capillaries, adaptors for transferring the nanoreactor from the system to the detection device, etc.

In some embodiments, a thermal history indicator is disposable.

Thermal history indicator kits are also provided herein. A thermal history indicator kit may include a metal precursor component and a carrier component. The metal precursor component may include any of the metal precursors disclosed herein while the carrier component may include any of the carriers disclosed herein. A thermal history indicator kit may include a metal precursor component and a carrier component, wherein the metal precursor component and the carrier component are located in separate compartments in the kit, and wherein the metal precursor component and the carrier component could be mixed so as to produce a nanoreactor. The mixing of the metal precursor component and the carrier component may be performed at room temperature or at temperatures below or above room temperature, for example, 90° C. The metal precursor and carrier components may exist in different states, including, but not limited to, liquids, gels, solids, powders, gases, etc.

In some embodiments, the metal precursor and carrier components both are liquids. In some embodiments, the metal precursor component is a solid and the carrier component is a liquid. In some embodiments, the metal precursor component is a liquid and the carrier component is a solid.

Some illustrative embodiments of thermal history indicator kits are shown in FIGS. 28 and 29. The separate compartments for the metal precursor component and the carrier component of a thermal history indicator kit may exist in different configurations. In some embodiments, the metal precursor component and the carrier component are in compartments that are physically separated. As shown in FIG. 28A, thermal history indicator kit 10 may include a metal precursor component compartment 12 that is a separate compartment from the carrier component compartment 14. In such embodiments, a nanoreactor may be produced by transferring the contents, entirely or partially, from the metal precursor compartment 12 to the carrier compartment 14 or vice versa.

In some embodiments, the metal precursor component and the carrier component are in compartments that are adjacent to one another but separated by a removable barrier. As shown in FIG. 28B, a thermal history indicator kit 10 may include a metal precursor component compartment 12 that is adjacent to the carrier component 14 and separated by a removable barrier 16. The removable barrier 16 (shown in FIGS. 28 and 29) may be made of any material that can physically separate the metal precursor compartment from the carrier compartment and be removable so as to allow an opening between the metal precursor compartment and the carrier compartment. In one embodiment, the barrier may be a gel made from a high concentration of the carrier that can be melted by heating and mixed to create the nanoreactor. Removal of the barrier may occur by any of several types of mechanisms known in the art, including, but not limited to, physical removal, heating, etc.

In some embodiments, the metal precursor component and the carrier component could be mixed so as to produce any one of the nanoreactors described herein. In some embodiments, the metal precursor component is a 10 mM $HAuCl_4$ solution and the carrier component is a 0.0025 g/mL chitosan solution. In such exemplary embodiments, the metal precursor component and carrier components are mixed to create a final nanoreactor comprising 1 mM $HAuCl_4$ and about 0.0025 g/mL. In some embodiments, the metal precursor component is a 10 mM $HAuCl_4$ solution and the carrier component is a 0.01 g/mL alginic acid solution. In such exemplary embodiments, the metal precursor component and carrier components are mixed to create a final nanoreactor comprising 1 mM $HAuCl_4$ and about 0.01 g/mL.

A thermal history indicator kit may also include a first metal precursor+carrier component and a second metal precursor component. The first and second metal precursors may include any of the metal precursors disclosed herein while the carrier may include any of the carriers disclosed herein. A thermal history indicator kit may include a first metal precursor+carrier component and a second metal precursor component, wherein the first metal precursor+carrier component and the second metal precursor component are located in separate compartments in the kit, and wherein the first metal precursor+carrier component and the second metal precursor component could be mixed so as to initiate a nanoreactor. The mixing of the first metal precursor+carrier component and the second metal precursor component may be performed at room temperature or at temperatures below or above room temperature, for example, 90° C. The first metal precursor+carrier component and the second metal precursor component may exist in different states, including, but not limited to, liquids, gels, solids, powders, gases, etc. In some embodiments, the first metal precursor+carrier component and the second metal precursor component both are liquids. In some embodiments, the first metal precursor+carrier component is a solid and the second metal precursor component is a liquid. In some embodiments, the first metal precursor+carrier component is a liquid and the second metal precursor component is a solid.

Figure 29A:
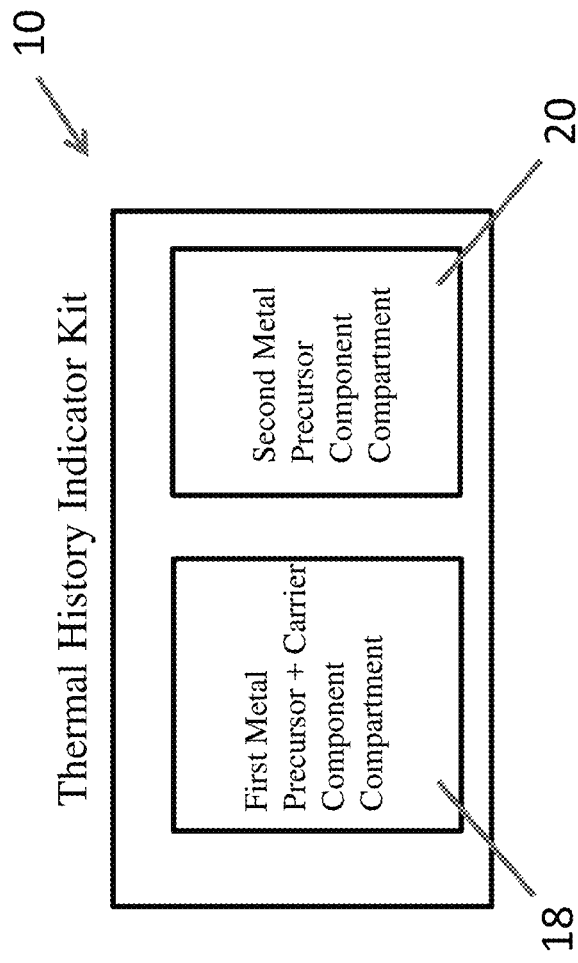
FIGS. 29A-E show exemplary embodiments of a thermal history indicator kit comprising two metal precursors.

The separate compartments for the first metal precursor+carrier component and the second metal precursor component of a thermal history indicator kit may exist in different configurations. In some embodiments, the first metal precursor+carrier component and the second metal precursor component are in compartments that are physically separated. As shown in FIG. 29A, thermal history indicator kit 10 may include a first metal precursor+carrier component compartment 18 that is a separate compartment from the second metal precursor component compartment 20. In such embodiments, a nanoreactor may be produced by transferring the contents, entirely or partially, from the first metal precursor+carrier component compartment 18 to the second metal precursor component compartment 20 or vice versa.

Figure 29B:
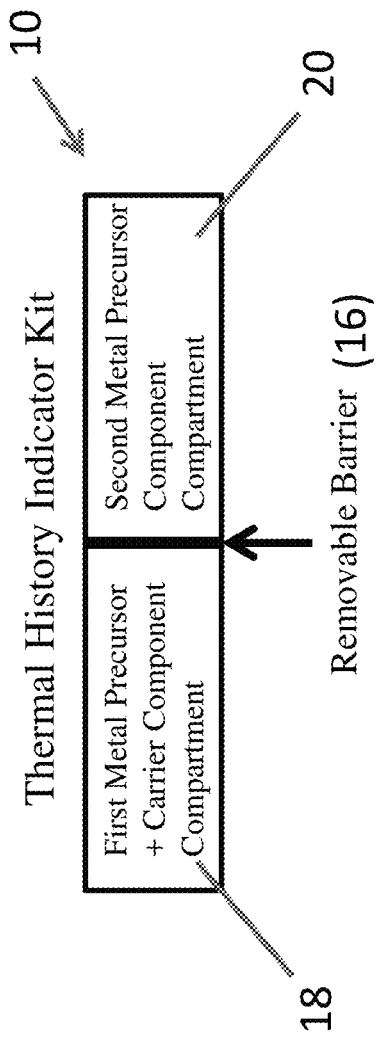

In some embodiments, the first metal precursor+carrier component and the second metal precursor component are in compartments that are adjacent to one another but separated by a removable barrier. As shown in FIG. 29B, a thermal history indicator kit 10 may include a first metal precursor+carrier component compartment 18 that is adjacent to the second metal precursor component compartment 20 and separated by a removable barrier 16.

Figure 29C:
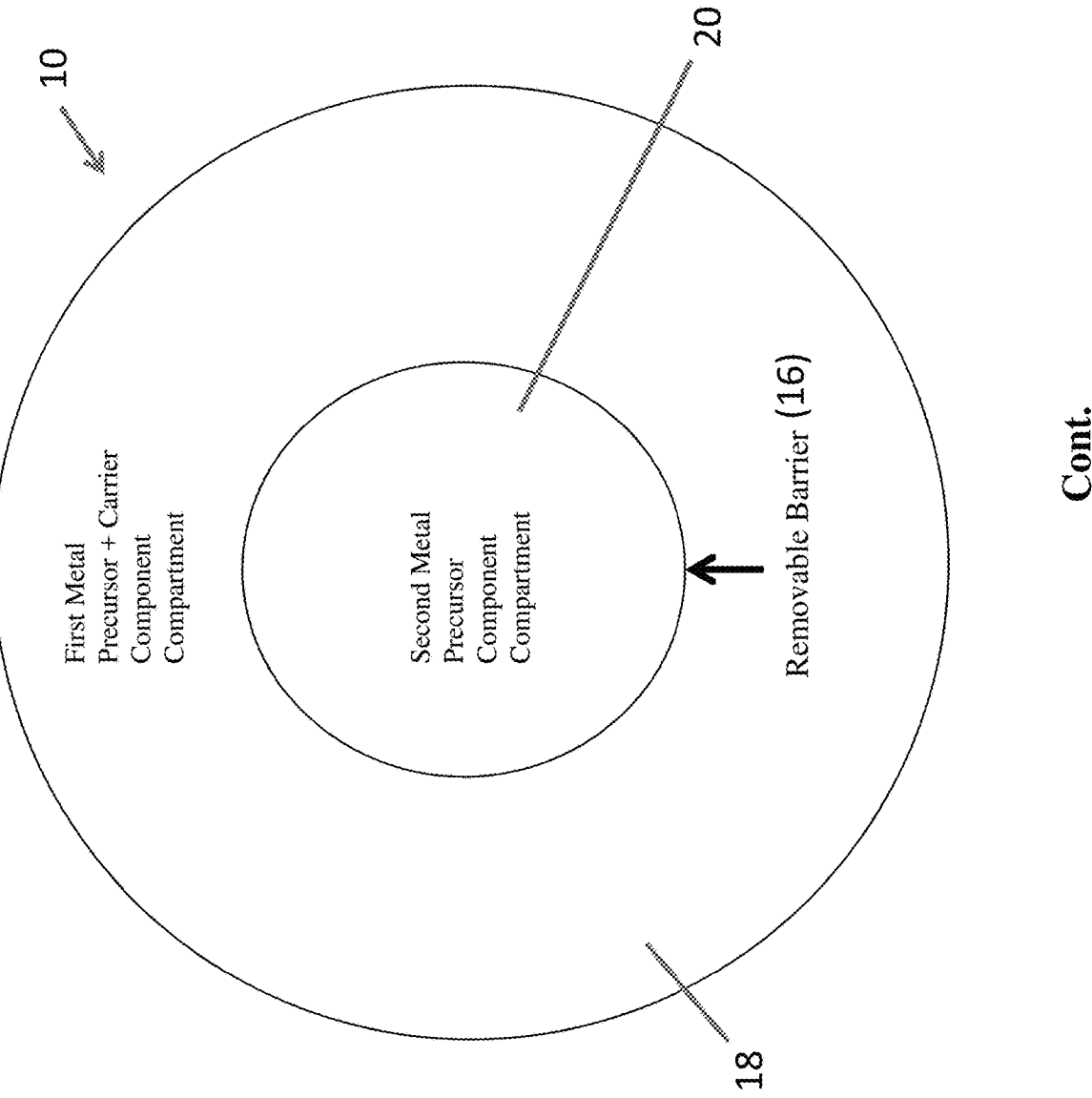

In some embodiments, the first metal precursor+carrier component and the second metal precursor component are in compartments that are concentric circles (or any other shapes such as squares, rectangles, triangles, etc.) to one another but separated by a removable barrier. As shown in FIG. 29C, a thermal history indicator kit 10 may include a first metal precursor+carrier component compartment 18 that encloses the second metal precursor component compartment 20 but is separated by a removable barrier 16. Of course, it will be readily appreciated by those in the art that the compartments shown in FIG. 29C may be switched such that the second metal precursor component compartment 20 encloses the first metal precursor+carrier component compartment 18. Additionally, it will be appreciated that thermal history indicator kits including metal precursor component and a carrier component, as described above and in FIG. 28, or the thermal history indicator kits including a carrier component, a first metal precursor component, and a second metal precursor component, as described below and in FIGS. 29 D-E, may also be configured into thermal history indicator kits as shown in FIG. 29C.

A thermal history indicator kit may also include a first metal precursor component, a second metal precursor component, and a carrier component. The first and second metal precursor components may include any of the metal precursors disclosed herein while the carrier component may include any of the carriers disclosed herein. The first metal precursor component, second metal precursor component, and the carrier component may be located in separate compartments in the kit and could be mixed so as to initiate or create a nanoreactor. The mixing of the first metal precursor component, second metal precursor component, and the carrier component may be performed at room temperature or at temperatures below or above room temperature, for example, 90° C. The first metal precursor component, second metal precursor component, and the carrier component may exist in different states, including, but not limited to, liquids, gels, solids, powders, gases, etc. In some embodiments, the first metal precursor component, second metal precursor component, and the carrier component are all liquids. In some embodiments, the first metal precursor component and carrier component are a solid and the second metal precursor component is a liquid. In some embodiments, the first metal precursor component and carrier component is a liquid and the second metal precursor component is a solid.

Figures 29D, 29E:
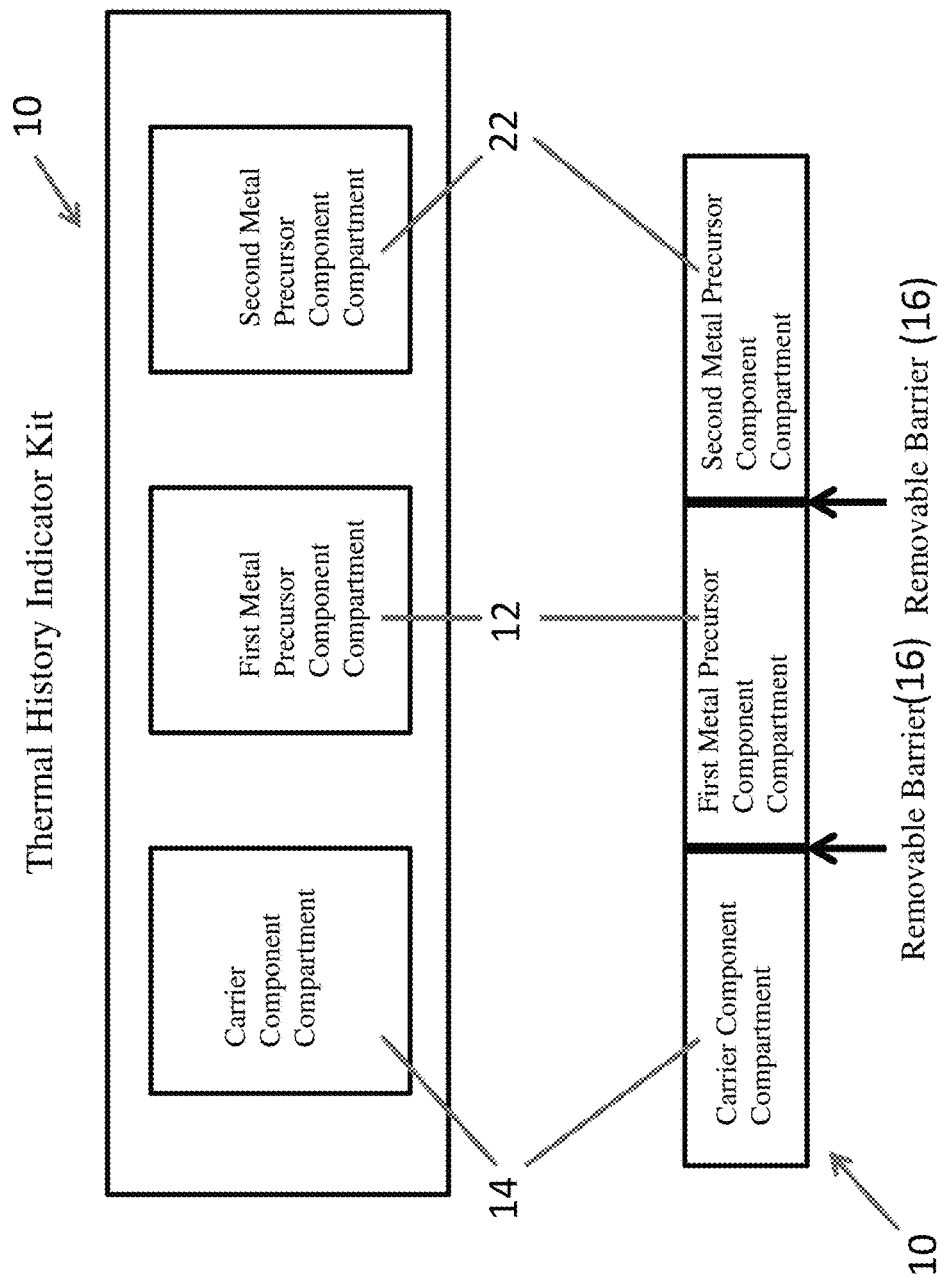

The separate compartments for the first metal precursor component, a second metal precursor component, and a carrier component of a thermal history indicator kit may exist in different configurations. In some embodiments, the first metal precursor component, second metal precursor component, and a carrier component are in compartments that are physically separated. As shown in FIG. 29D, thermal history indicator kit 10 may include a carrier component compartment 14, a first metal precursor compartment 12, and a second metal precursor compartment 22 that are all separate compartments. In such embodiments, a nanoreactor may be produced by transferring the contents, entirely or partially, from the carrier component compartment 14 to the first metal precursor compartment 12 and then, when initiation is desired for example, to the second metal precursor component compartment 22 or any combination thereof.

In some embodiments, the first metal precursor component, a second metal precursor component, and a carrier component are in compartments that are adjacent to one another but separated by a removable barrier. As shown in FIG. 29E, a thermal history indicator kit 10 may include a carrier component compartment 14, a first metal precursor compartment 12, and a second metal precursor compartment 22 that are adjacent to one another and separated by a removable barrier 16.

Exemplary Methods for Preparing Nanoreactors

Methods for preparing nanoreactors are provided herein. The methods may include preparing any one of the nanoreactors described herein at a temperature between 20° C. and 30° C. In some embodiments, the methods may include preparing a nanoreactor, heating the nanoreactor to between 70° C. and 95° C. for between 1 and 60 minutes, and cooling the nanoreactor to 30° C. or below. In some embodiments, any one of the nanoreactors described herein may be prepared, heated to between 70° C. and 95° C. for between 1 and 60 minutes, and cooled to 30° C. or below. In some embodiments, a method for preparing nanoreactors comprises preparing a nanoreactor, heating the nanoreactor to about 90° C. for between 2.5 and 15 minutes, and cooling the nanoreactor to 4° C. or below prior to using the nanoreactor as a THI.

Exemplary Methods of Using Nanoreactors

Methods of determining the thermal history of a nanoreactor are provided. In some embodiments, such methods comprise detecting at least one characteristic of the nanoreactor and based on the characteristic determining whether the nanoreactor was exposed to an undesired temperature for a time period, wherein the nanoreactor was placed at a storage temperature for a time regime. In some embodiments, the nanoreactor used may be any one of the nanoreactors described herein.

In some embodiments, a nanoreactor comprises gold precursor present at a concentration between 0.1 mM and 10 mM, gelatin present at a concentration between 0.001 g/mL and 0.03 g/mL, and water, wherein the nanoreactor was prepared by incubation at a temperature between 70° C. and 95° C. for between 1 and 60 minutes, and wherein the time regime is more than 45 days. In some embodiments, a nanoreactor comprises gold precursor present at a concentration between 0.1 mM and 10 mM, gelatin present at a concentration between 0.0005 g/mL and 0.03 g/mL, and water, wherein the nanoreactor was prepared by incubation at a temperature between 20° C. and 30° C. (Preferably room temperature).

Methods of detecting exposure of a perishable good to an undesired temperature are also provided. Such methods comprise, in some embodiments, exposing said perishable good to a storage temperature for a time regime wherein the perishable good is packaged in association with a nanoreactor, detecting at least one characteristic of the nanoreactor, and based on the characteristic determining whether the perishable good was exposed to an undesired temperature for a time period during storage.

In some embodiments, the nanoreactor used may be any one of the nanoreactors described herein.

In some embodiments the time regime is between 12 hours and 365 days, or between 45 and 365 days, or is more than 45 days, or is not more than 125 days.

In some embodiments, the storage temperature is between −100° C. and 25° C., or between −40° C. and 0° C., or about −20° C., or about 4° C. In some embodiments, the storage temperature is between 20° C. and 30° C. In some embodiments, the storage temperature may be about −20° C., about 0° C., about 4° C., about 23° C., or about room temperature and the methods described herein may be used to detect temperature changes of at least 5, 10, 15, 20, 25, 30, 35, 40, 45, 50, 55, 60, 65, 70, 75, 80, 85, 90, 95, or 100 degrees centigrade below or above the storage temperature that occur for at least 10 minutes, 20 minutes, 30 minutes, 45 minutes, 1 hour, 2 hours, 5 hours, 10 hours, 15 hours, 24 hours, 2 days, 5 days, 10 days, 15 days, 20 days, 25 days, or 30 days.

In some embodiments, the undesired temperature is between −20° C. and 90° C., or between 20° C. and 90° C., or between 20° C. and 40° C. In some embodiments, the undesired temperature is between −50° C. and 10° C.

In some embodiments, the time period is between 10 minutes and 2 months, or is between 10 minutes and 48 hours, or is between 60 minutes and 24 hours, or between 2 hours and 48 hours.

In some embodiments, the perishable good is a perishable biologic. For example, it is widely known that biologics such as proteins or polypeptides must generally be stored at temperatures below 5° C. or they will degrade and/or lose their functional activity. It is envisioned that the nanoreactors and methods described herein could be used to detect whether biologics were exposed to elevated temperatures during, for example, transportation. In the Examples, the inventors have shown that the disclosed nanoreactors may be used to monitor a storage temperature of about −20° C. or about 4° C. and detect temperature abuses of as little as 1, 2, 4, 6, 8, 10, 12, or 24 hours at either room temperature or 40° C. (See FIG. 13). Therefore, when associated with perishable goods such as biologics, the disclosed nanoreactors may be used as thermal history indicators (by either examining the color or absorbance) that would signal to an end user whether the perishable good was exposed to an undesired temperature thus compromising the quality of the perishable good.

In some embodiments, detecting at least one characteristic of the nanoreactor comprises detecting a characteristic selected from color, peak wavelength, peak shape, absorbance, nanoparticle size, nanoparticle size distribution, and nanoparticle number. In some embodiments, detecting at least one characteristic of the nanoreactor comprises detecting color.

Detection of at least one characteristic of the nanoreactor may be by any suitable method. Exemplary detection methods include, but are not limited to, visible inspection, UV-VIS spectrophotometry, scanning electron microscopy (SEM), transmission electron microscopy (TEM), dynamic laser scattering (DLS), x-ray radiography, digital image processing (DIP), and atomic force microscopy (AFM).

In some embodiments, when the characteristic to be detected is color, visual inspection and/or UV-VIS spectrophotometry is selected as a detection method.

In some embodiments, when the characteristic to be detected is peak wavelength and/or peak absorbance and/or peak shape, UV-VIS spectrophotometry is selected as a detection method. In some embodiments, when a peak wavelength and/or peak absorbance and/or peak shape is to be detected and the nanoreactor comprises gold precursor, a spectrum that includes at least 530 nm to 550 nm is taken. In some embodiments, a spectrum from 400 nm to 800 nm is taken.

In some embodiments, the absorbance of one or more individual wavelengths is determined. In some such embodiments, at least one wavelength is a wavelength between 530 nm and 550 nm. In some such embodiments, at least one wavelength is selected from 530, 531, 532, 533, 534, 535, 536, 537, 538, 539, 540, 541, 542, 543, 544, 545, 546, 547, 548, or 550 nm.

In some embodiments, when the characteristic to be detected is nanoparticle size, suitable detection methods include, for example, DLS, SEM, TEM, AFM, x-ray radiography, and digital image processing (DIP) of the images obtained from, e.g., SEM and TEM.

In some embodiments, when the characteristic to be detected is nanoparticle shape, suitable detection methods include, for example, SEM, TEM, AFM, UV-visible spectroscopy, x-ray radiography, and DIP of the images obtained from, e.g., SEM and TEM.

In some embodiments, when the characteristic to be detected is nanoparticle number, suitable detection methods include, for example, DLS and x-ray radiography.

In some embodiments, when the characteristic to be detected is nanoparticle size distribution, suitable detection methods include, for example, DLS and x-ray radiography.

One skilled in the art can select a suitable detection method depending on the characteristic(s) of the nanoreactor and/or nanoparticles that are to be detected. The selected method need not be a method specifically listed above.

In some embodiments, a detection method includes the use of a standard. One skilled in the art can devise a suitable standard according to the particular detection method, detection location, user, nanoreactor system, use of the nanoreactor system, etc. The purpose of the standard is to allow interpretation of the time and temperature to which to nanoreactor in association with the perishable good was exposed. The standard may be a set of similar nanoreactors exposed to a wide variety of temperatures for various periods of time to which the nanoreactor can be compared. The standard may be developed in advance of the nanoreactor being placed in association with the perishable good to allow for a later comparison between the nanoreactor and the standard.

When the detection method is visual inspection of nanoreactor color, in some embodiments, a standard may comprise one or more colors to which the color of the nanoreactor can be compared. The one or more color standards may be in any form, such as colors printed on paper, plastic, cardstock, etc.; or colored samples that have a similar appearance to the nanoreactor. By "similar appearance," it is meant, in some embodiments, that the samples have similar viscosity and/or opacity and/or are packaged in similar containers as the nanoreactor. The samples, in some embodiments, are not themselves nanoreactors, but samples that mimic the appearance of a nanoreactor that has been exposed to certain time/temperature conditions. In some embodiments, a color standard comprises more than one color such that a nanoreactor can be compared to the color standard and by identifying the color closest to the color of the nanoreactor, the time/temperature conditions experienced by the nanoreactor can be estimated.

When the detection method is UV-Vis spectrophotometry, in some embodiments, a standard may be one or more samples that produce similar spectra as nanoreactors that have experienced various time/temperature conditions. In some embodiments, a standard may be a document showing one or more peak wavelengths and/or peak absorbances of nanoreactors that have experienced certain known time/temperature conditions.

In some embodiments, the methods of determining the thermal history of a nanoreactor and methods of detecting exposure of a perishable good to an undesired temperature further comprise comparing the detected characteristic of a nanoreactor to a standard. With any detection method, a standard comprising a known number, shape, size, and/or size distribution of nanoparticles may be used. In some embodiments, a standard is generated by subjecting a nanoreactor to particular conditions, such as in a laboratory. In some embodiments, one or more characteristics of the nanoreactor and/or nanoparticles of the standard are detected using one or more methods described above. In some embodiments, the output of that detection is then used as standard. That is, for example, in some embodiments, a UV/visible spectrum taken of a standard nanoreactor subjected to particular conditions is used as standard against which UV/visible spectra of nanoreactors in use are compared. In some embodiments, multiple standards are used. In some embodiments, when multiple standards are used, one or more of the multiple standards are based on nanoreactors that have been subjected to different particular conditions. In some embodiments, when multiple standards are used, one or more of the multiple standards show different characteristics of one or more nanoreactors that have been subjected to different particular conditions. One skilled in the art can select a suitable standard according to the intended use of the nanoreactors.

For the methods of detecting exposure of a perishable good to an undesired temperature, a nanoreactor is associated with a perishable good when it is present in a thermal history indicator and within the packaging of the perishable good, included in a container with one or more units of the perishable good, anchored to a container holding one or more units of the perishable good, or otherwise present in such a location that the nanoreactor is expected to experience a similar environment as the perishable good. In some embodiments, a similar environment is a similar temperature environment. In some embodiments, a container holds multiple smaller containers, each of which holds multiple units of the perishable good. In some such embodiments, a nanoreactor can be associated with a unit of the perishable good, with the smaller container, or with the container holding multiple smaller containers. That is, the nanoreactor may be included in, or anchored to, a unit of the perishable good, such as in a box in which the perishable good is provided to consumers; or it may be included in, or anchored to, a container holding multiple units of the perishable good; or it may be included in, or anchored to, a container holding multiple such smaller containers that hold multiple units of the perishable good, etc.

In some embodiments, a nanoreactor is included in the same container as the perishable good. For example, in some embodiments, a nanoreactor is included inside a glass or plastic container that also holds the perishable good. In some such embodiments, the nanoreactor is visible through a wall of the glass or plastic container. In some embodiments, whether or not the nanoreactor is visible, it is present in a known location such that microparticles in the nanoreactor can be detected by a particular method without opening the container that holds the perishable good.

In some embodiments, the presence of nanoparticles in the nanoreactor can be detected after first removing the nanoreactor from the location where it is (or was) associated with the perishable good or reaction (the perishable good or reaction need not still be present at the time the nanoreactor is removed and detected). In some embodiments, the detection is done in situ—from the location where it is (or was) associated with the perishable good (again, the perishable good or reaction need not still be present at the time the nanoreactor is detected).

In some embodiments, the location of the nanoreactor that is associated with a perishable good or reaction is known such that nanoparticles in the nanoreactor can be detected without first removing the nanoreactor from the location where it is (or was) associated with the perishable good or reaction. As a nonlimiting example, a nanoreactor may be anchored to the inside of a container holding the perishable good or reaction. In some embodiments, the location of the nanoreactor is known and/or indicated on the outside of the container. Nanoparticles in the nanoreactor can be detected, e.g., using x-ray radiography even though the nanoreactor is not visible to an outside observer.

The presently described nanoreactors provide a way of detecting exposure of a perishable good to an undesired temperature. The color (i.e. hue and/or intensity), peak wavelength, and/or peak absorbance of the nanoreactor; as well as the size, number, size distribution and/or shape of the nanoparticles formed in the nanoreactor, provide information on the temperature to which the nanoreactor has been exposed, and the duration of the exposure to that temperature.

Further, in some embodiments, by using appropriate standards as discussed above, one skilled in the art can determine the temperatures to which a perishable good has been exposed, and estimate the duration of that exposure.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as between 1 and 10 (units), it is intended that ranges such as between 2 and 9 (units), between 3 and 8 (units) etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the claims. All references cited herein are hereby incorporated by reference in their entireties.

EXAMPLES

Example 1—Gelatin-Based Nanoreactors

Gelatin-Based Thermal History Indicators (THIs) for Monitoring Low-Temperature Storage Reagents Hydrogen tetrachloroaurate (III) trihydrate ($HAuCl_4 \cdot 3H_2O$) and gelatin type A powder were purchased from Acros Organics. Both chemicals were used as received without any purification, and all aqueous solutions were prepared in deionized Millipore water (resistivity>18 MΩ·cm).

Preparation of Gelatin-Based Thermal History Indicators (THIs)

Gold precursor solution (10 mM) was prepared by dissolving $HAuCl_4$ in water. Gelatin solution was also prepared by stirring gelatin powder in water for 30 min at 90° C. for complete dissolution. In a typical procedure, 0.1 v/v gold precursor solution is mixed with the gelatin solution and heated in a water bath at 90° C. for 10 min under constant stirring, and 1 mL of this mixture is placed in 1.5-mL cuvettes, which constituted THIs. The effects of heating temperature (70, 80, and 90° C. for 60 min), heating time (1 to 60 min), and gelatin concentration (0.01, 0.02, 0.04 $g \cdot mL^{-1}$) were investigated.

Evaluation of Gelatin-Based THIs

The THIs prepared under optimal set of experimental conditions were evaluated for their performance subjecting them to different storage temperature regimes presented in FIG. 1. One set of THIs were exposed to room temperature (RT=23° C.) for 0, 2, 4, 8, 12 and 24 h before being stored in a freezer at −20° C. for a total of 90 days. These THIs were designated as RT-0 h to RT-24 h, with the number representing the duration the THIs were at room temperature prior to frozen storage. A second set of THIs was left at room temperature for 90 days, without ever being stored in the freezer; this was denoted as RT-90d. The color of all THIs were examined by monitoring their absorbance spectra using PerkinElmer, Lambda 25 UV/Vis spectrophotometer. The morphology of the nanoparticles was imaged using FEI Tecnai T12 transmission electron microscope (TEM) operating at 120 kV. Typically, one drop of sample was placed on a carbon-coated 400-mesh copper grid and excess solution was removed by wicking with filter paper. The grid was allowed to dry at RT before imaging. Particle size analysis was performed on at least 50 particles observed in the TEM images using Olympus Soft Imaging Viewer software and the particle size characteristics (mean diameter and standard deviation) were determined.

Results

Heating Temperature and Heating Time

Heating temperature and duration are important parameters during the preparation of THIs. As shown in FIG. 7, the synthesis of AuNPs commences sooner at higher heating temperature (90° C.), which is accompanied by the appearance of pinkish color [13]. Also, for the same heating duration, the color of THIs becomes more intense at higher heating temperature. The peak shift in localized surface plasmon resonance (LSPR) in the UV-vis spectra is consistent with the color change of the THIs. Therefore, 90° C. was chosen as the optimal temperature for the preparation of THIs as it takes less time.

Furthermore, at any given temperature, the pinkish color of THIs became more intense with time, which is more easily observed at 90° C. (FIG. 7). The TEM images show that the average size of AuNPs decreased with increasing heating duration (FIG. 2). However, there are a large number of tiny particles, some of which grow larger with heating time. This could explain why the color of THIs continues to grow more intense with increased heating time. As we had reported [14], during heating the reduction of gold precursor continues to progress, causing many small nuclei to form new particles or leading the existing small particles to attach to other larger particles. As a result, the size dispersion increases with heating time, from 4.2 nm (20 min of heating) to 7.0 nm (60 min of heating). The average size and standard deviation of AuNPs determined from the TEM images are listed in Table 1.

TABLE 1

Average size and size dispersion of AuNPs within different heating time of THIs

| Heating time (min) | Partice size (nm, mean ± std. dev.; n = 50) |
| --- | --- |
| 20 | 19.5 ± 4.2 |
| 40 | 16.3 ± 6.8 |
| 60 | 13.5 ± 7.0 |

The UV-vis spectra show that the peak wavelength of the samples heated for 10 to 60 min are all ~537±1 nm (FIG. 8B, ESM); however, the amplitude of the spectra increased, which imply more nanoparticles are being synthesized [15]. Although some particles become larger, since the average size did not increase, the LSPR peak of the AuNPs did not show an obvious red-shift during this heating period. Moreover, typically a blue-shift in the LSPR peak is associated with either decomposition of large nanoparticles into smaller ones or change in the crystallinity of the nanoparticles [15]. Since the LSPR peaks did not show a blue-shift, we consider that the formation of many small particles during heating is not at the cost of few larger particles being decomposed. We continue to investigate the changes in crystallinity to more fully understand the reasons for these observed changes in the LSPR.

Gelatin Concentration

Figures 3A, 3B, 3C:
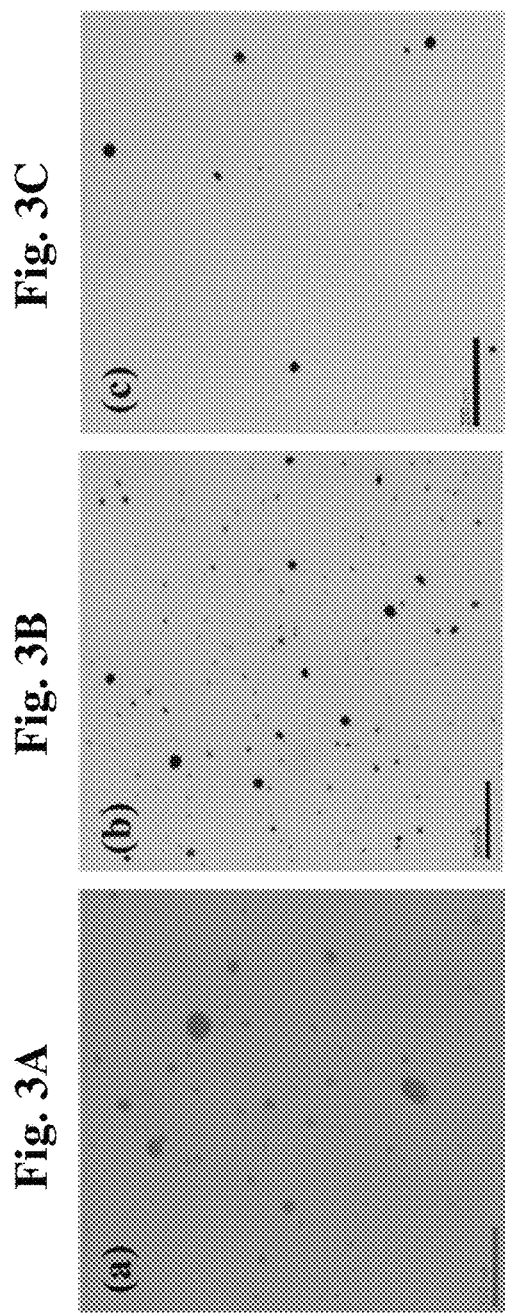
(FIG. 3A) 0.01, (FIG. 3B) 0.02, and (FIG. 3C) 0.04 after 30 min of heating at 90° C.
Figure 7A:
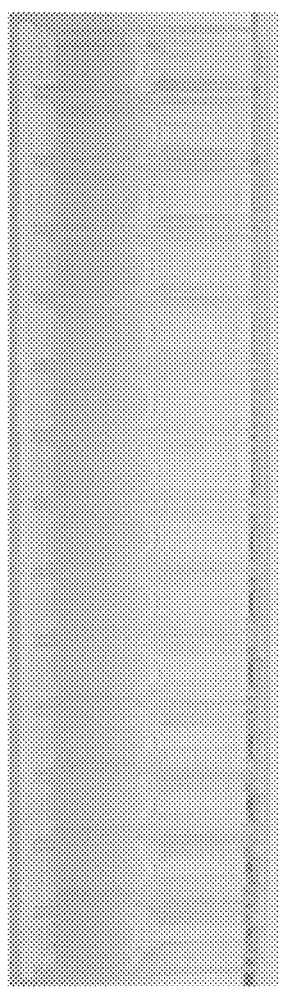
(FIG. 7A) 70° C., (FIG. 7B) 80° C., and (FIG. 7C) 90° C. From left to right, sample color changed during heating at 4 min intervals from 8 to 60 min.
Figure 7B:
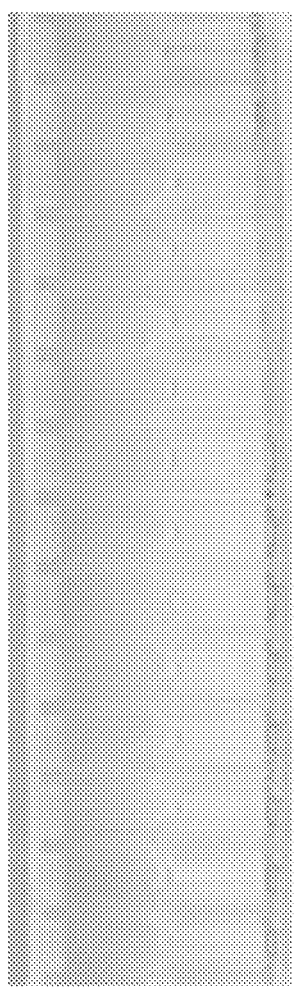
FIG. 7 shows nanoreactors synthesized (using 0.1 v/v 10 mM of $HAuCl_4$ with 0.02 g/mL gelatin) at different temperatures.
FIG. 7F shows nanoreactors including 0.1 v/v 10 mM $HAuCl_4$ with different gelatin concentrations (left to right: 0.01, 0.02, and 0.04 g/mL) heated at 90° C. for 30 min.
Figure 7C:
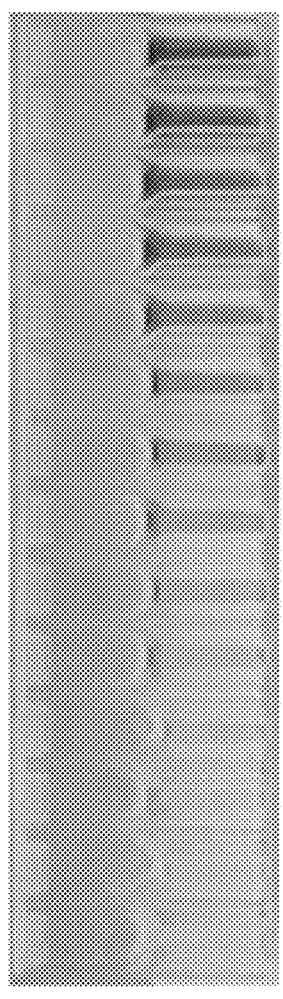
Figure 7D:
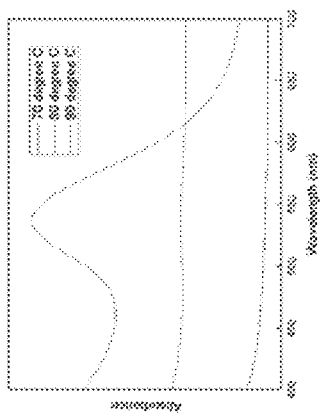
Figure 7E:
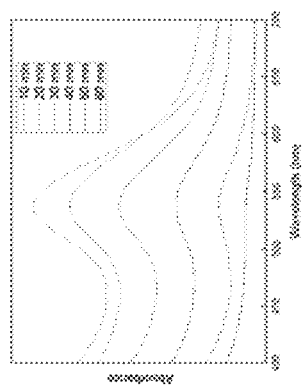
Figure 7F:
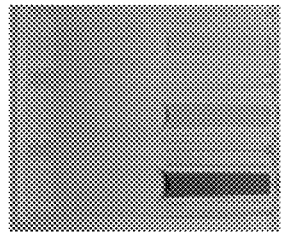

Under the same heating regime, the THIs containing 0.01 g·mL−1 of gelatin produced the deepest purple color; whereas, the system with 0.04 g·mL−1 gelatin failed to develop the typical pinkish/purplish color (FIG. 7F). We premise that the high viscosity of the THIs with high gelatin content hindered the growth of AuNPs. The TEM images (FIG. 3), which show larger particles in THIs containing 0.01 g·mL−1 of gelatin than in those containing 0.02 and 0.04 g·mL−1 of gelatin, corroborate this speculation. Although higher gelatin concentration could facilitate increased reduction of the gold precursor solution, the growth of AuNPs is more favored in systems with lower gelatin concentration. However, to better distinguish the color change by the bare eye and better observe the time- and temperature-dependent growth of AuNPs, we need to choose a gelatin concentration that would not result in too fast or too slow a synthesis and growth of AuNPs. The THIs with 0.01 g·mL−1 gelatin produced too dark an initial color for further color development and visual observation; while the THIs with 0.04 g·mL−1 gelatin yielded too slow a rate of AuNPs synthesis. Hence, we chose 0.02 g·mL−1 as the optimal gelatin concentration for the preparation of THIs.

Evaluation of THIs

The UV-vis spectra of the samples (FIG. 4A) show a gradual shift in the LSPR of AuNPs—the longer the exposure of THIs at RT, the greater the red-shift. For example, comparing RT-0 h and RT-24 h, after 90 days of storage, their peak wavelength has red-shifted from 538 to 546 nm. The corresponding colors of the THIs are also visibly distinguishable (FIG. 4A inset). These results suggest the potential for tracking temperature history based on system color and color intensity.

The just-synthesized THIs is light pink in color, perhaps due to the presence of AuNPs [13], which are fairly spherical with an average particle size of 18.9±3.4 nm (FIG. 4B). After 90 days of frozen storage, both the size and shape of AuNPs changed. Although some of the particles are irregularly shaped, many pentagonal and hexagonal particles were observed in the TEM images of different THIs. While we continue to investigate the mechanism for shape evolution, previous studies have suggested that time might be the key factor [16, 17].

The average size of AuNPs increased with the duration of exposure to RT, which perhaps corresponds to the change in the LSPR. Thus, we believe that duration of exposure of THIs at RT could be related to the particle size and hence the color intensity. This was confirmed by the UV-vis spectra and color (FIG. 4C) and the size of AuNPs (FIG. 4D) in RT-90d. The UV-vis spectrum of RT-90d has red-shifted to 572 nm with much larger amplitude compared to that of RT-0 h, whose LSPR peak is at 538 nm. This is an indication that more AuNPs have been synthesized [15].

Figures 5A, 5B:
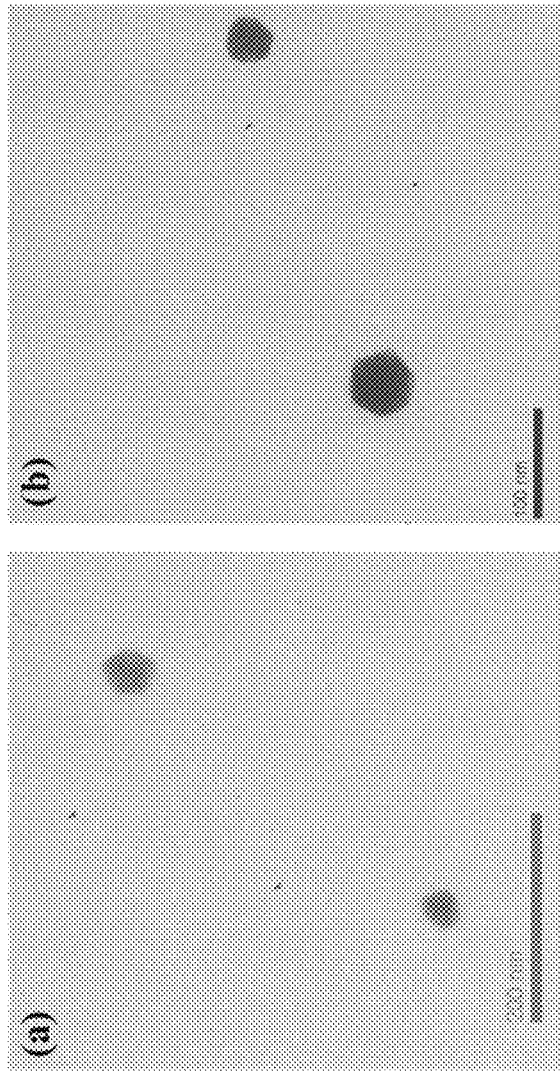
FIG. 5 shows TEM images of the gold nanoparticles in THIs (0.1 v/v 10 mM of $HAuCl_{4+0.02}$ g·mL$^{-1}$ gelatin and heated at 90° C. for 10 min) after storage at room temperature for (FIG. 5A) 2 h and (FIG. 5B) 24 h followed by in a freezer at −20° C. for 90 days.

The TEM images of RT-90d (FIG. 4D) show many hexagonal/hexagonal-like AuNPs are seen; however, its average particle size is much larger than those in RT-0 h (FIG. 4B). Since the only difference between these two THIs is the temperature during storage, temperature is the key contributor to the size of AuNPs, which validates our previous suggestion, i.e., the longer the exposure of THIs to room temperature, the larger the size of the average AuNPs. Even 24 h of exposure to room temperature, compared to 2 h exposure, resulted in larger AuNPs (FIG. 5). The longer exposure to room temperature perhaps increases the reducing effect of gold precursor.

Figure 6:
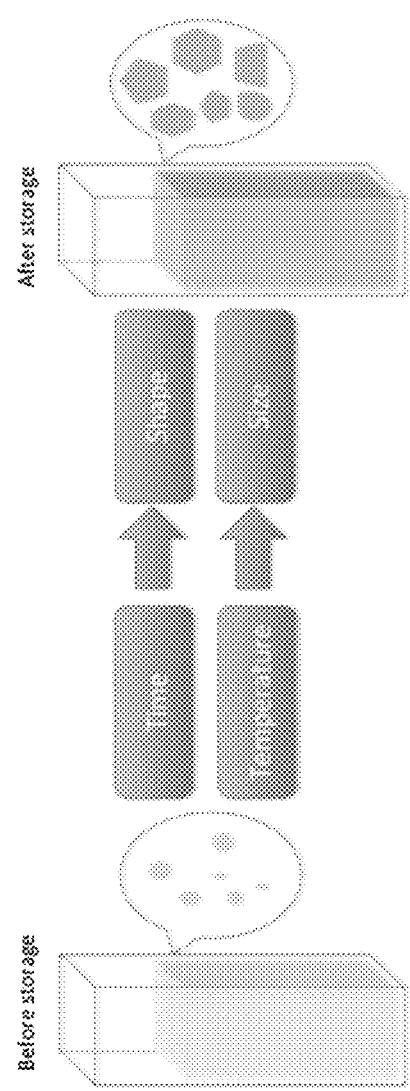
FIG. 6 shows an illustration of AuNPs size and shape evolution in THIs exposed to different storage times and temperatures. Generally, in our system, the size change is mainly due to storage temperature and the shape change due to storage time.

Thus, the color/UV-vis spectra of the THIs, is a function of both storage time and temperature (FIG. 6), which demonstrates the potential of THIs as a system for tracking thermal history of perishable foods, high-value biological and pharmaceutical products. Compared to several reported THIs (Table 2), the tested THI is simpler to fabricate and use over a wider range of temperatures and for longer storage periods, which is necessary for monitoring time-temperature abuse in products during low-temperature storage.

We used gelatin as a reducing agent and stabilizer to control the particle growth to prepare AuNPs-based THIs that are suitable for monitoring product quality and/or safety of food and biomaterials during low-temperature storage. The THI preparation parameters, heating temperature, heating time, and gelatin concentration, were optimized. We consider THI systems containing 0.1 v/v 10 mM of HAuCl4 and 0.02 g·mL−1 of gelatin heated for 10 min at 90° C. to be the optimal for visually observing color changes during low-temperature (freezer to room temperature) storage. The THIs that were at room temperature for longer time exhibited deeper color along with more red-shifted LSPR peak of AuNPs. By comparing the TEM images and the UV-vis spectra of the AuNPs, our results demonstrate that the size and shape of the AuNPs are mainly the result of storage temperature and time, respectively. These THIs afford a proactive way for tracking time-temperature history of perishable foods and biomaterials by visual color change, and hence provide objective traceability information to determine quality and/or safety of products.

REFERENCES FOR EXAMPLE 1

1. Galmés A, Besalduch J, Bargay J, Novo A, Morey M, Guerra J M, Duran M A (1999) Long term storage at −80° C. of hematopoietic progenitor cells with 5-percent dimethyl sulfoxide as the sole cryoprotectant. Transfusion 39:70-73
2. Moog R, Knopp D, Wenzel F (2010) Temporary storage of fresh frozen plasma above −30° C. has no negative impact on the quality of clotting factors and inhibitors. TransfusAltern TransfusMed 11:8-9
3. Derwood P, Aleksandar M (2007) Storage of hemopoietic stem cells. Asian J Transfus Sci 1(2):71-76
4. Hoffmann S, Batz M B, Morris J J G (2012) Annual cost of illness and quality-adjusted life year losses in the United States due to 14 foodborne pathogens. J Food Prot 75:1292-1302
5. Tao H, Brenckle M A, Yang M, Zhang J, Liu M, Siebert S M, Averitt R D, Mannoor M S, McAlpine M C, Rogers J A, Kaplan D L, Omenetto F G (2012) Silk-based conformal. Adhes Edible Food Sensors Adv Mater 24:1067-1072
6. Raviyan P, Tang J, Orellana L, Rasco B (2003) Physicochemical properties of a time temperature indicator based on immobilization of *Aspergillus oryzae* α-amylase in polyacrylamide Gel as affected by degree of cross-linking agent and salt content. J Food Sci 68:2302-2308

TABLE 2

Comparison of different THIs reported in the literature

| Method/Mechanism | Matrix | Temperature Range[a] | Time Regime[a] and notes | Ref. |
|---|---|---|---|---|
| Enzyme-based | *Aspergillus oryzae* α-amylase in polyacrylamide gel | 7-65° C. | The enzyme activity may reduce with time | [6] |
| Dye-based | 4,4'-Bis(2-benzoxazolyl) stilbene/ethylene/norbornene copolymer | 130-200° C. | Tunable between seconds and days | [7] |
| Phase Separation | Amide aqueous solution/sodium chloride | Tunable from −10 to 60° C. | Once exposed to a certain temperature threshold, the phase separation reaction begins. (It may only work at one specific temperature at a time.) | [8] |
| Diffusion | Lactic acid | 4 to 45° C. | Within 1 week | [18] |
| LSPR[b] | Ag/Au nanorods | 10 to 35° C. | About 3 days | [10] |
| LSPR | Gelatin/AuNPs | −20° C. up to 90° C. | At least 90 days | This work |

[a]Per experimental data reported
[b]Localized Surface Plasmon Resonance

7. Sing C E, Kunzelman J, Weder C (2009) Time-temperature indicators for high temperature applications. J Mater Chem 19:104-110
8. Kitsunai M, Miyajima K, Mikami Y, Kim S, Hirasawa A, Chiba K (2008) Phase-separable aqueous amide solutions as a thermal history indicator. Biosci Biotechnol Biochem 72:3314-3317
9. Wang X, Wolfbeis O S, Meier R J (2013) Luminescent probes and sensors for temperature. Chem Soc Rev 42:7834-7869
10. Zhang C, Yin A-X, Jiang R, Rong J, Dong L, Zhao T, Sun L-D, Wang J, Chen X, Yan C-H (2013) Time-Temperature indicator for perishable products based on kinetically programmable Ag overgrowth on Au nanorods. ACS Nano 7:4561-4568
11. Won Y-W, Yoon S-M, Sonn C H, Lee K-M, Kim Y-H (2011) Nano self-assembly of recombinant human gelatin conjugated with α-tocopheryl succinate for Hsp90 inhibitor, 17 AAG. Deliv ACS Nano 5:3839-3848
12. Lim S, Gunasekaran S, Imm J Y (2012) Gelatin-templated gold nanoparticles as novel time-temperature indicator. J Food Sci 77:N45-N49
13. Ray P C (2010) Size and shape dependent second order nonlinear optical properties of nanomaterials and their application in biological and chemical sensing. Chem Rev 110:5332-5365
14. Wang Y-C, Gunasekaran S (2012) Spectroscopic and microscopic investigation of gold nanoparticle nucleation and growth mechanisms using gelatin as a stabilizer. J Nanopart Res 14:1-11
15. Sardar R, Shumaker-Parry J S (2011) Spectroscopic and microscopic investigation of gold nanoparticle formation: ligand and temperature effects on rate and particle size. J Am Chem Soc 133:8179-8190
16. Petroski J M, Wang Z L, Green T C, El-Sayed M A (1998) Kinetically controlled growth and shape formation mechanism of platinum nanoparticles. J Phys Chem B 102:3316-3320
17. Burda C, Chen X, Narayanan R (2005) Chemistry and properties of nanocrystals of different shapes. Chem Rev 105:1025-1102
18. Wanihsuksombat C, Hongtrakul V, Suppakul P (2010) Development and characterization of a prototype of a lactic acid-based time-temperature indicator for monitoring food product quality. J Food Eng 100:427-434

Formation of Gelatin-Based Nanoreactors at Room Temperature

Figures 8A, 8B, 8C, 8D:
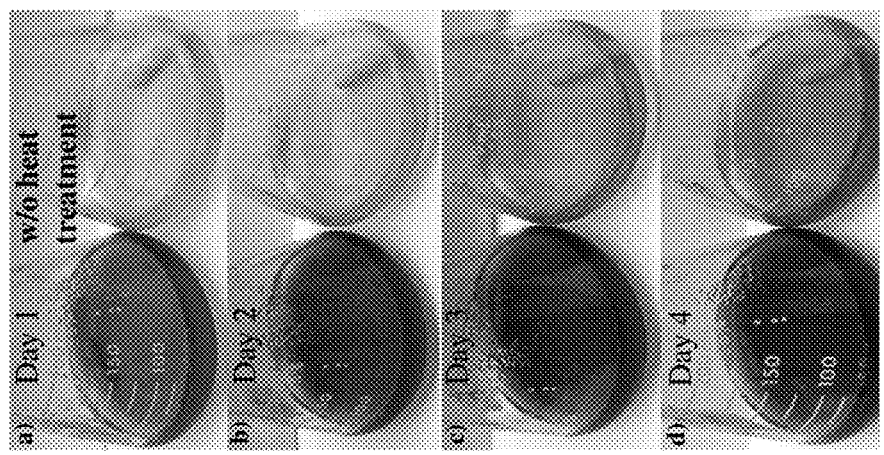
FIGS. 8A-D show the colors of the nanoreactors over a 4 day period. These results suggest AuNPs are synthesized in a gelatin/gold precursor system at room temperature, though at a much slower rate, and suggests that the nanoreactor can be composed just before its use, which can serve as a starting switch and prior heat treatment of the reactor is not necessary.

Gelatin-based nanoreactors may be formed at room temperature (FIG. 8). To demonstrate that nanoreactors may be formed at room temperature, we prepared a nanoreactor comprised of 0.02 g. mL$^{-1}$ of gelatin with 1 mM HAuCl$_4$ and heated at 90° C. for 15 min before being placed at room temperature (Left in FIG. 8). We also prepared a nanoreactor comprised of 0.02 g. mL$^{-1}$ of gelatin with 1 mM HAuCl$_4$ and placed it at room temperature (Right in FIG. 8). The colors of the nanoreactors were then monitored over a 4 day period (FIGS. 8A-D). As can be seen in FIG. 8, the color of each nanoreactor changed over time. The results suggest AuNPs are synthesized in a gelatin/gold precursor system at room temperature, though at a much slower rate, and suggests that the nanoreactor can be composed just before its use, which can serve as a starting switch.

Example 2—Chitosan-Based Nanoreactors

Reagents

Hydrogen tetrachloroaurate (III) trihydrate (HAuCl4·3H2O) and chitosan were purchased from Acros Organics. Both chemicals were used as received without any purification, and all aqueous solutions were prepared in deionized Millipore water (resistivity>18 MΩ·cm).

Preparation of Chitosan-Based Nanoreactors

Chitosan-based nanoreactors were synthesized by mixing 10 mM of hydrogen tetrachloroaurate (HAuCl$_4$) with various chitosan solutions having 0.0625%, 0.125%, and 0.25% chitosan (on a w/w basis) and continuously stirring the mixture at 90° C. for 15 minutes. The final concentrations in the chitosan nanoreactors were 1 mM HAuCl$_4$ and 0.0625%, 0.125%, or 0.25% chitosan.

Results

Properties of the Chitosan-Based Nanoreactors

Figure 9A:
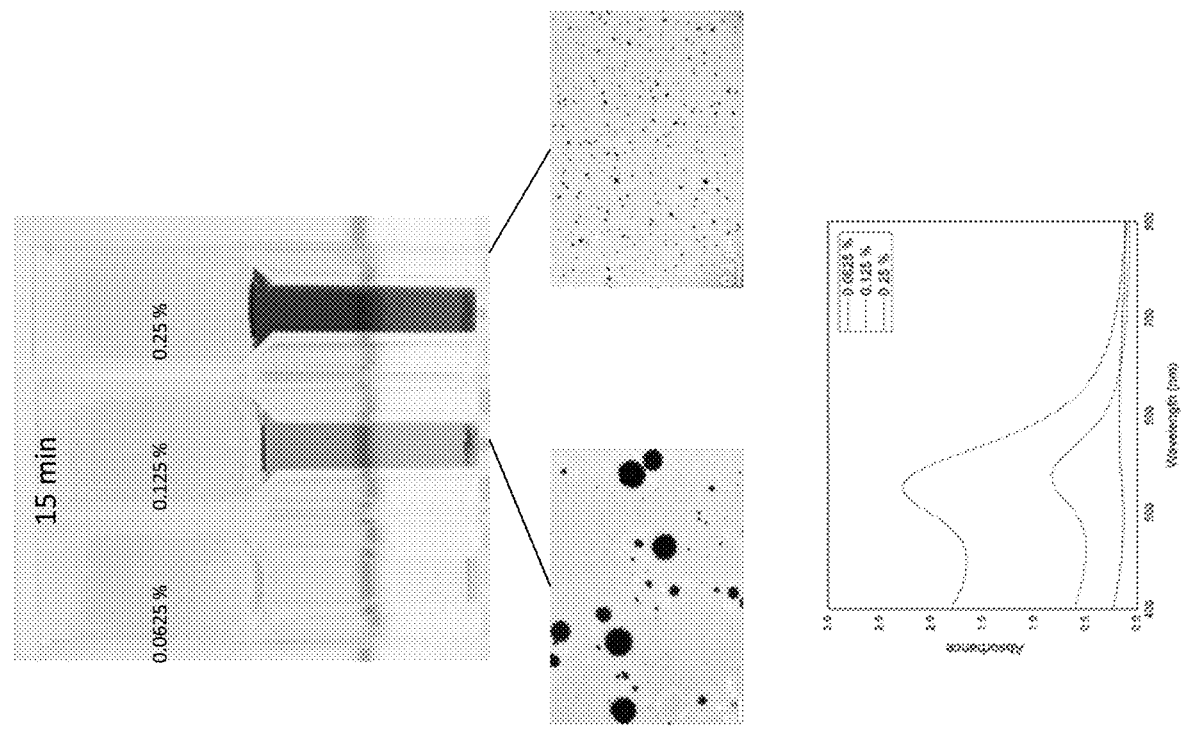
In FIG. 9A the reactions were heated for 15 min.
Figure 9B:
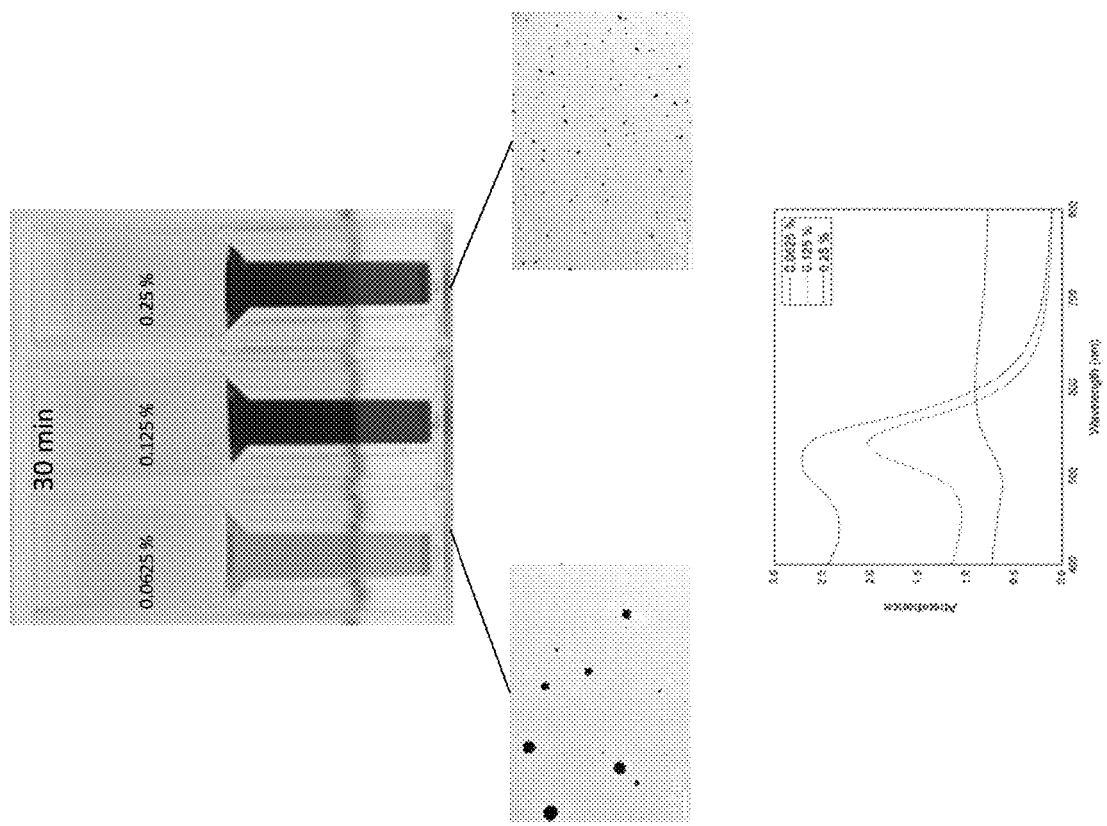
In FIG. 9B the reactions were heated for 30 min.
Figure 10:
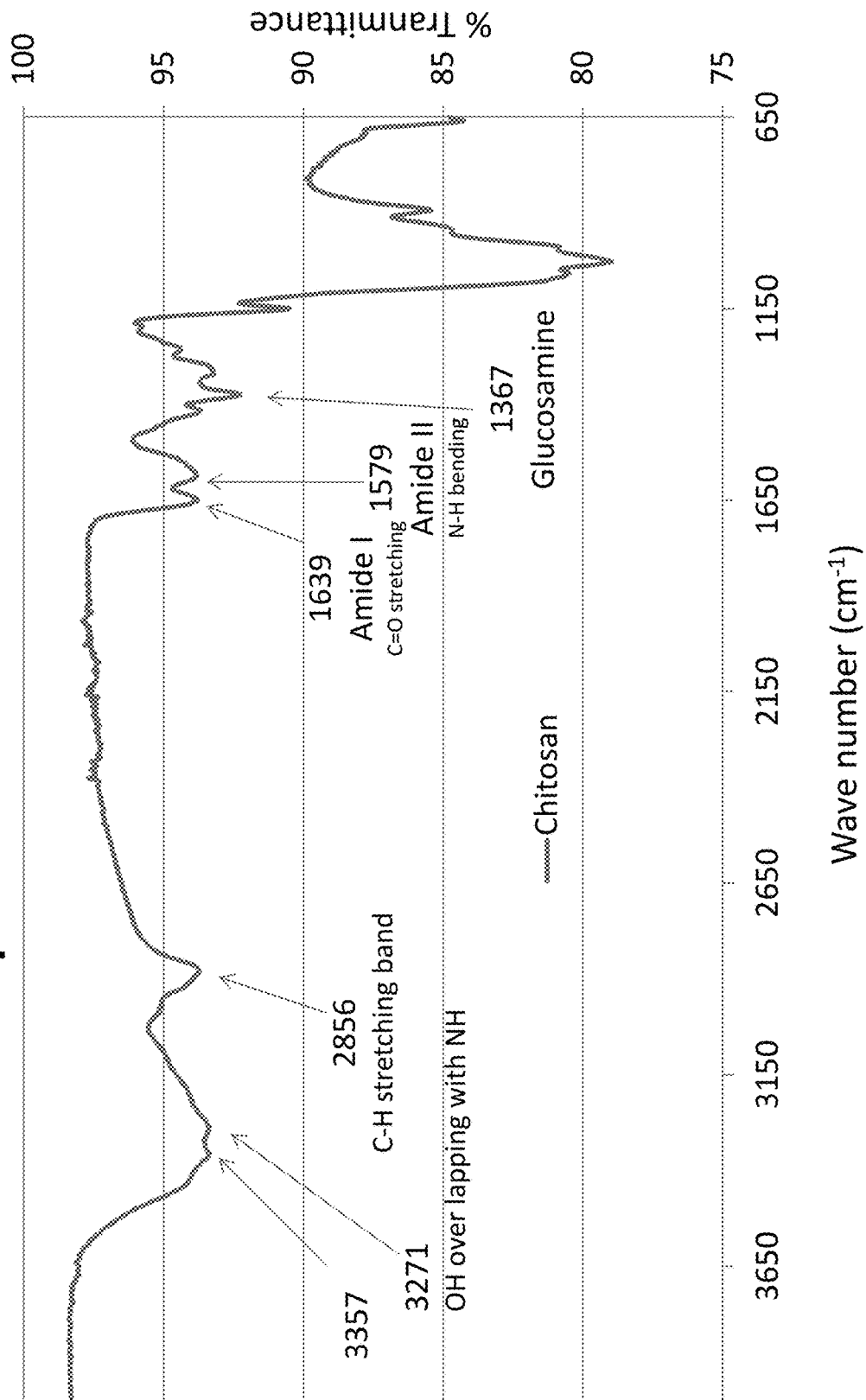
FIG. 10 shows FTIR spectra of chitosan.
Figure 11A:
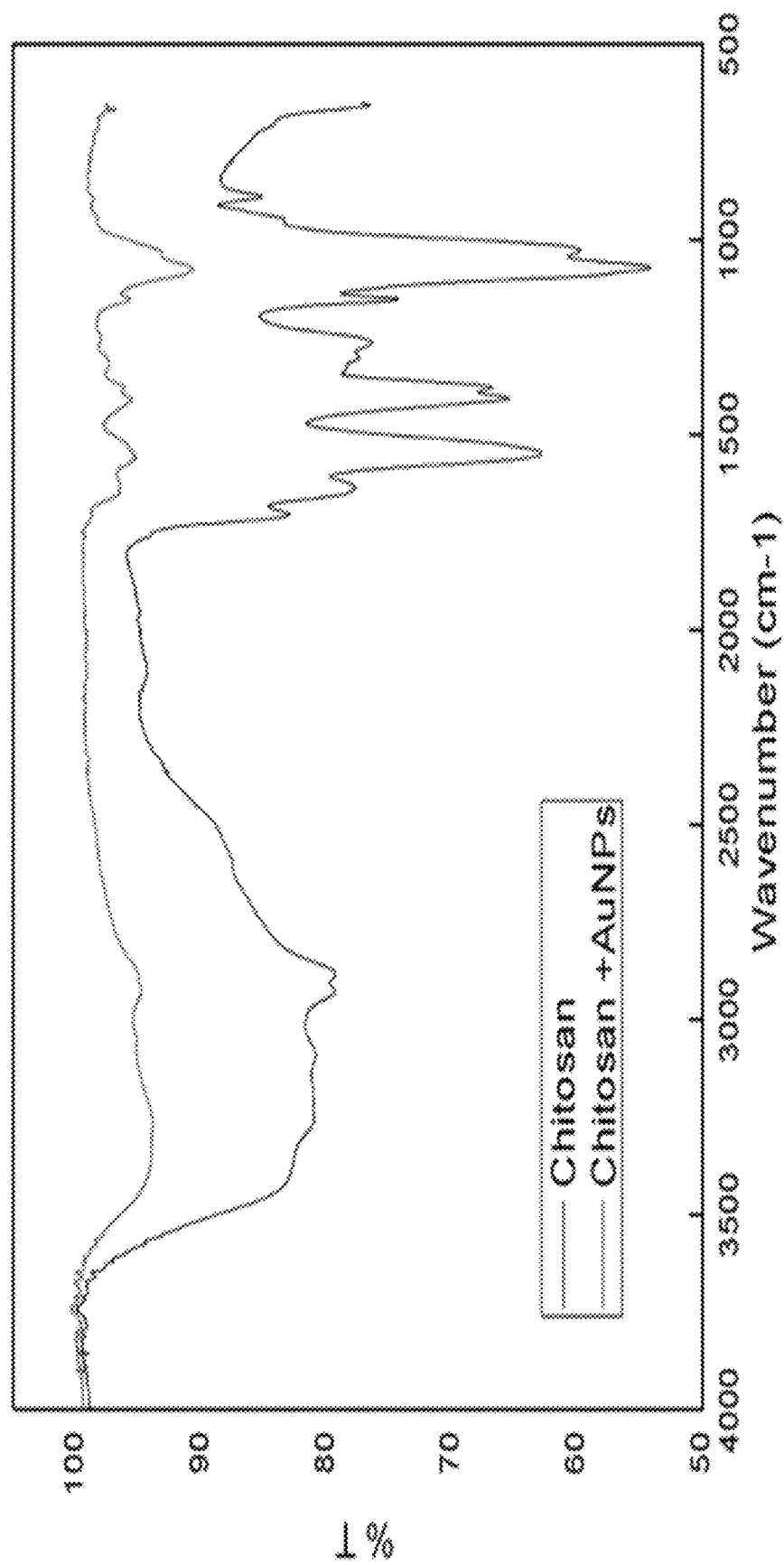
FIG. 11A shows FTIR spectra of chitosan and chitosan/AuNPs nanoreactors prepared by mixing 1 mM of $HAuCl_4$ with 0.25% of chitosan solution and heating at 90° C. for 30 min.
Figure 11B:
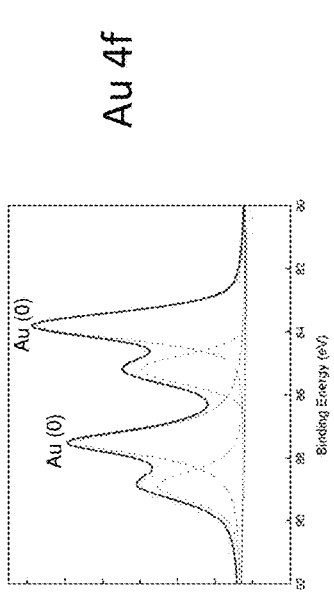
FIG. 11B shows the core level Au 4f XPS spectra of chitosan/AuNPs nanoreactors.
Figure 11C:
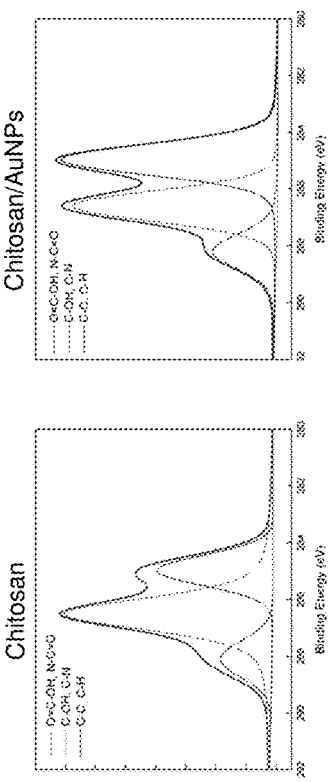
FIG. 11C shows the core level C 1s XPS spectra of chitosan/ and chitosan/AuNPs nanoreactors.
Figure 11D:
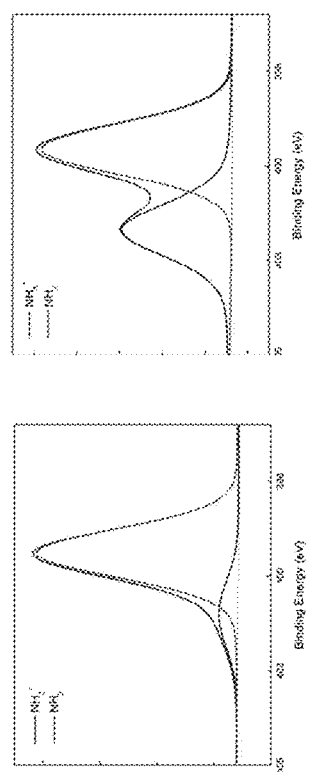
FIG. 11D shows the core level N 1s XPS spectra of chitosan/ and chitosan/AuNPs nanoreactors.

Chitosan-based nanoreactors (0.0625%, 0.125%, and 0.25% chitosan) were analyzed using several techniques. The color of the initial chitosan-based nanoreactors were visually inspected; and UV-Visible spectra and TEM images were determined (FIGS. 9A and 9B). Several additional parameters of chitosan-based nanoreactors were also determined by DLS (Table 3) as well as FTIR spectra and XPS measurements for both chitosan (FIG. 10) and chitosan-based nanoreactors (FIGS. 11A-11D).

TABLE 3

| Parameters | Chitosan (0.0625%) | Chitosan (0.125%) | Chitosan (0.25%) |
| --- | --- | --- | --- |
| Effective diameter (nm) | 175.6 ± 1.28 | 59.8 ± 1.49 | 30.6 ± 1.17 |
| Polydispersity | 0.233 | 0.209 | 0.247 |
| Zeta potential (mV) | 64.24 ± 2.78 | 58.58 ± 3.08 | 51 ± 2.18 |

Properties of the Chitosan-Based Nanoreactors Under Frozen Conditions

The behaviors of chitosan-based nanoreactors at −18° C. over various periods of time (0, 7, 15, 21, 29 days) was determined by DLS (Table 4).

TABLE 4

| | Effective diameter (nm) | | |
| --- | --- | --- | --- |
| Time (Days) | Chitosan (0.0625%) | Chitosan (0.125%) | Chitosan (0.25%) |
| 0 | 175.6 ± 1.28 | 59.8 ± 1.49 | 30.6 ± 1.17 |
| 7 | 176.8 ± 2.04 | 62.4 ± 1.18 | 30.9 ± 1.82 |
| 15 | 178.4 ± 1.67 | 61.3 ± 2.04 | 31.8 ± 1.08 |
| 21 | 173.8 ± 2.18 | 67.5 ± 1.56 | 33.7 ± 1.77 |
| 29 | 180.9 ± 2.44 | 69.1 ± 1.92 | 34.2 ± 1.88 |

Chitosan Nanoreactors for Cold Detection

Figure 12:
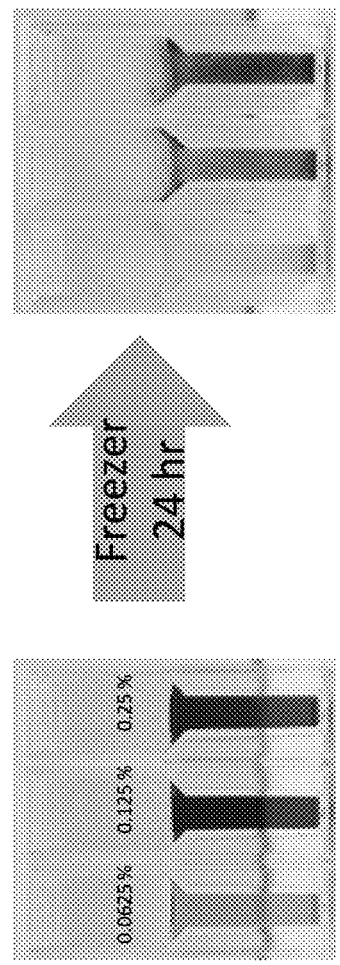
FIG. 12 shows that chitosan-based nanoreactor may be used for freezing detection. An initial nanoreactor comprising 0.0625%, 0.125%, or 0.25% of Chitosan with 1 mM $HAuCl_4$ was heated at 90° C. for 30 minutes. The nanoreactor was then placed in a freezer (−20° C.) for 24 hours.

Chitosan-based nanoreactor may be used for cold detection (FIG. 12). To test chitosan-based nanoreactors in cold detection, we prepared an initial nanoreactor comprising 0.125% of Chitosan with 1 mM HAuCl$_4$ and heated the nanoreactor at 90° C. for 30 minutes. The nanoreactor was then placed in a freezer (−20° C.) for 24 hours. After 24 hours, the nanoreactor exhibited a clear color change from a reddish color to a light purple grayish color.

Temperature Abuse Studies with Chitosan Nanoreactors

We have also performed temperature abuse studies using chitosan-based nanoreactors (FIG. 13). To determine the sensitivity of chitosan-based nanoreactors to different periods of temperature abuse, we prepared chitosan-based nanoreactors having 0.2%, 0.25%, or 0.3% chitosan plus 1 mM of HAuCl$_4$ and heated at 90° C. for 15 min. The nanoreactors were then stored in −20° C. freezer for 2 days, then placed at RT for 0-24 hr, followed by returning to −20° C. for 1 additional day (FIGS. 13A-13C) or were stored in −20° C. freezer for 2 days, then placed at 40° C. for 0-24 hr, followed by returning to −20° C. for 1 additional day (FIGS. 13D-13F). We then observed the colors of the nanoreactors and measured the UV-spectra of some of the nanoreactors (FIGS. 13G and 13H) or produced TEM images of some of the nanoreactors (FIG. 13I). As can be seen in FIG. 12, significant differences in the color of the nanoreactor could be observed with as little as 1, 2, 4, 6, 8, 10, 12, or 24 hours of temperature abuse at either RT or 40° C. It can also been seen that the intensity of the color change correlated with the length of time spent at the abuse temperature such that the longer the time spent at the abuse temperature the deeper the color of the nanoreactor and greater the absorbance (including the peak absorbance). As shown in FIG. 13G, it was also observed that as the temperature abuse period increased, a shoulder between 600-700 nm may increase.

Example 3—Alginic Acid-Based Nanoreactors

Reagents

Hydrogen tetrachloroaurate (III) trihydrate ($HAuCl_4 \cdot 3H_2O$) and alginic acid (alginic acid sodium salt) were purchased from Acros Organics. Both chemicals were used as received without any purification, and all aqueous solutions were prepared in deionized Millipore water (resistivity>18 MΩ·cm).

Preparation of Alginic Acid-based Nanoreactors

Alginic acid-based nanoreactors with 1 mM of hydrogen tetrachloroaurate ($HAuCl_4$) with 0.01 g/mL of alginic acid solution at 90° C. for 2.5 minutes were prepared. The prepared mixture served as several nanoreactors, which were stored under different temperatures (0° C., 8° C. and room temperature for up to 24 hours). The initial color was transparent with no localized surface plasmon resonance (LSPR) peak.

Results

We also demonstrate that alginic acid-based nanoreactors may also serve as thermal history indicators (FIG. 14). An initial nanoreactor comprising 0.01 g·mL$^{-1}$ sodium alginate and 1 mM of $HAuCl_4$ was heated at 90° C. for 2.5 min (FIG. 14A). Portions of the initial nanoreactor were then placed at different temperatures (−20° C., 0° C., room temperature (RT), 40° C.) for two different periods of time (1 day or 5 days) and we monitored the color of the nanoreactor (FIGS. 14B and 14D) and measured the absorption spectrum of the nanoreactor (FIGS. 14C and 14E). The results demonstrate that alginic acid-based nanoreactors result in significantly different colors depending on the storage temperature and storage time period. At the molecular level, the nanoparticles within the nanoreactor also exhibited unique properties depending on the storage temperature and storage time period.

Figures 15A, 15B, 15C, 15D:
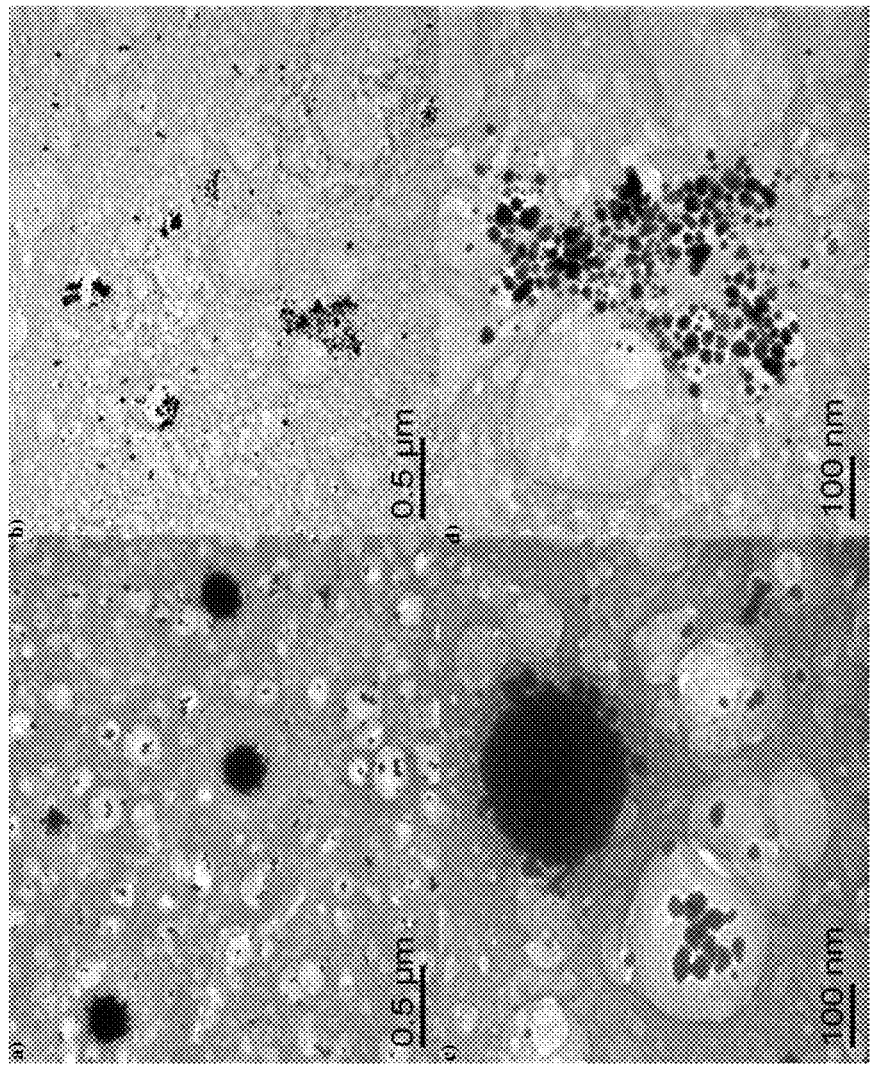
FIGS. 15A and 15C are TEM images of the nanoreactor shown in FIG. 14A after being at room temperature for 14 days.
FIGS. 15B and 15D are TEM images of the nanoreactor shown in FIG. 14A after being at 40° C. for 14 days.
Figure 16A:
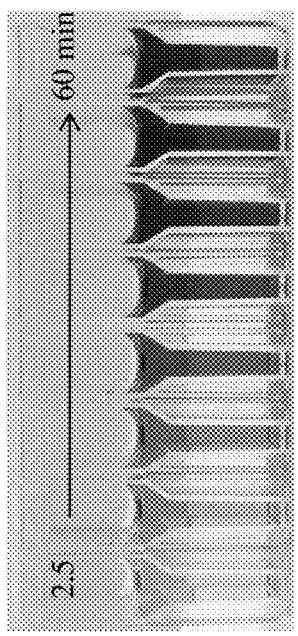
FIG. 16A shows a nanoreactor including 0.01 g·mL$^{-1}$ of alginate plus 1 mM of $HAuCl_4$, which was heated at 90° C. for 2.5 to 60 min.
Figure 16B:
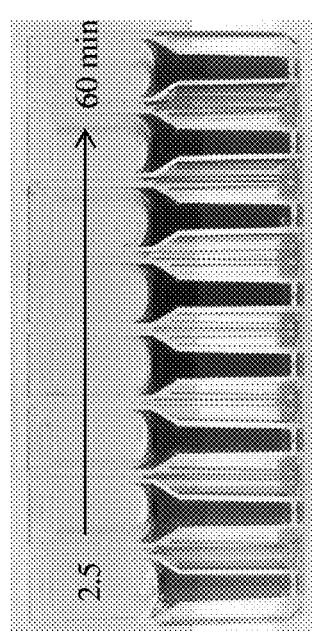
FIG. 16B shows a nanoreactor including 0.04 g·mL$^{-1}$ of alginate plus 1 mM of $HAuCl_4$, which was heated at 90° C. for 2.5 to 60 min.
Figure 16C:
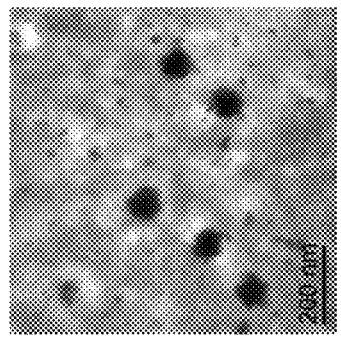
FIG. 16C shows a TEM image of a nanoreactor including 0.04 g·mL$^{-1}$ of alginate plus 1 mM of $HAuCl_4$, which was heated at 90° C. for 30 min.
Figure 16D:
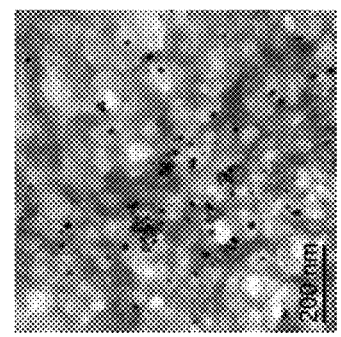
FIG. 16D shows a TEM image of 0.04 g·mL$^{-1}$ of alginate plus 1 mM of $HAuCl_4$, which was heated at 90° C. for 60 min.
Figure 16E:
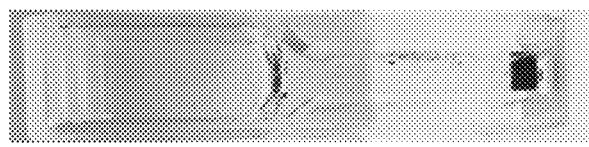
FIG. 16E shows a nanoreactor including 0.04 g·mL$^{-1}$ of alginate plus 1 mM of $HAuCl_4$, which was heated at 90° C. for 60 min and placed at 40° C. for 30 days.

As shown in FIG. 15, after storage under room temperature for 12 hours, TEM images showed some large particles (more than 200 nm) along with many smaller particles (less than 100 nm). Alginic acid-based nanoreactors prepared with different recipes also showed different sensitivities to the same storage condition. FIGS. 16 and 17 also show the effects of different alginic acid concentration on nanoreactor formation and color development.

We also demonstrate that divalent ions can solidify alginic acid-based nanoreactors to form gel or solid-based THI systems. For example, calcium ions can interact with the alginate biopolymer to form gels or solids (FIG. 18A). We prepared a thermal history indicator hydrogel prepared by adding 100 μL of 1% calcium chloride solution into 1 mL of the as prepared alginate-$HAuCl_4$ solution mixture (0.01 g·mL$^{-1}$ sodium alginate and 1 mM of $HAuCl_4$ heated at 90° C. for 2.5 min) which was stored at 0° C. for 2 h and exposure to room temperature (RT) for 0 (left) and 6 h (right) followed by storage at 0° C. for 24 h. The results suggest that the color thermal history indicator hydrogel also become deeper as the temperature abuse period becomes longer. As shown in FIG. 18B, alginic acid-based nanoreactors still exhibited a significant color change even when formed as a hydrogel comprising a divalent ion such as calcium.

Figure 19:
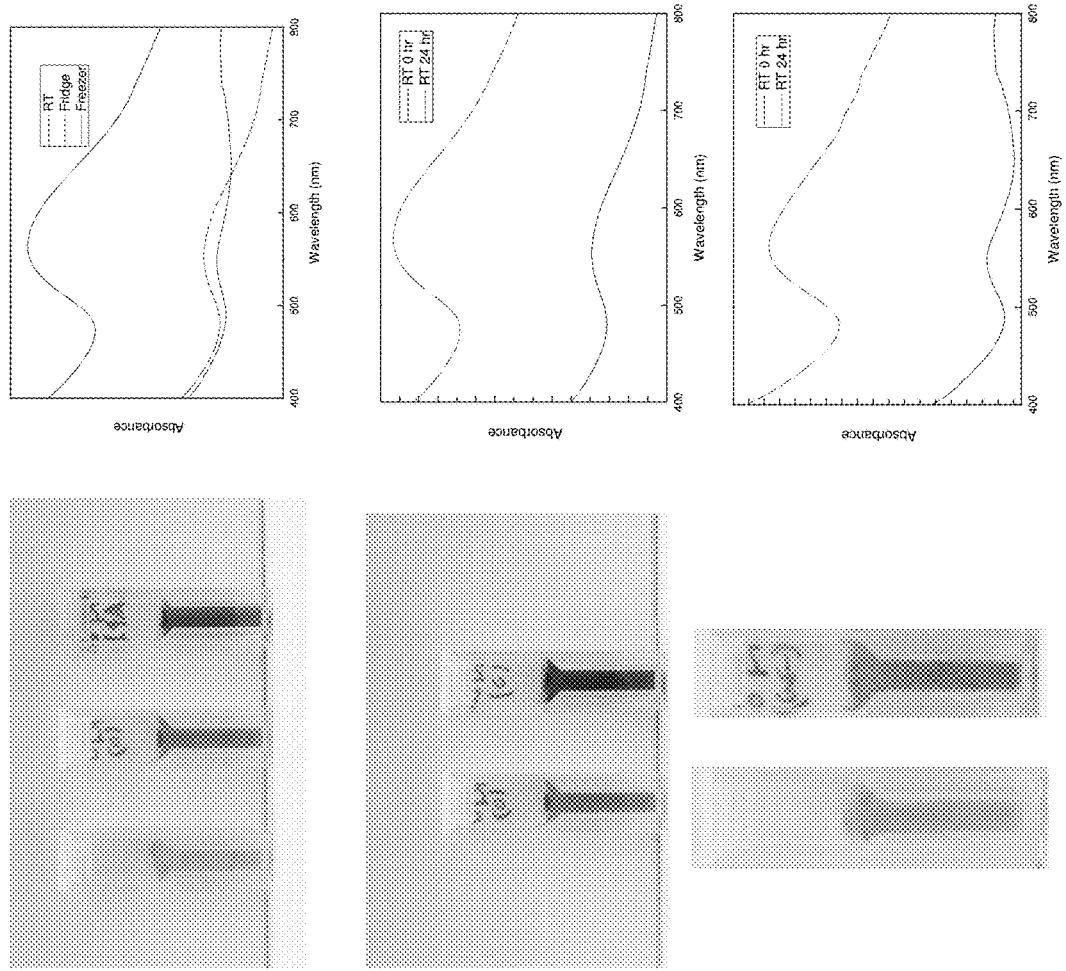
FIG. 19 shows alginic acid-based nanoreactors under different storage conditions and temperature abuse scenarios.

To determine the characteristics of alginic acid-based nanoreactors under different storage conditions, we prepared three nanoreactors by mixing 1 mM of hydrogen tetrachloroaurate ($HAuCl_4$) with 0.01 g/mL of alginic acid solution at 90° C. (FIG. 19A). Each nanoreactor was then stored at −20° C. (freezer), 0° C. (fridge), or RT for 50 hours and then the color of each nanoreactor (left) and UV-vis spectra (right) was determined. As can been seen in FIG. 19A, the color of the nanoreactor depended on the storage temperature.

We also tested the characteristics of alginic acid-based nanoreactors to different temperature abuse scenarios. To investigate storage at 0° C. with abuse at room temperature, we prepared two nanoreactors by mixing 1 mM of hydrogen tetrachloroaurate ($HAuCl_4$) with 0.01 g/mL of alginic acid solution at 90° C. (FIG. 19B). Each sample was stored at 0° C. for 2 hours, placed at room temperature for 0 or 24 hours, and then placed back to 0° C. for one additional day before measurement. We then determined the color and UV-vis spectra of each nanoreactor. As shown in FIG. 19B, the nanoreactor abused at room temperature for 24 hours had a deeper color than the nanoreactor that was not abused.

To investigate storage at −20° C. with abuse at room temperature, we prepared two nanoreactors by mixing 1 mM of hydrogen tetrachloroaurate ($HAuCl_4$) with 0.01 g/mL of alginic acid solution at 90° C. (FIG. 19C). Each sample was stored at −20° C. for 2 hours, placed at room temperature for 0 or 24 hours, and then placed back to −20° C. for one additional day before measurement. We then determined the color and UV-vis spectra of each nanoreactor. As shown in FIG. 19C, the nanoreactor abused at room temperature for 24 hours had a deeper color than the nanoreactor that was not abused.

Example 4—Nanoreactor Initiation and Multi-Stage Nanoreactors

The nanoreactor solution may be formed by synthesizing nanoparticles with the first metal precursor using any suitable reducing reagent, including, without limitation, sodium borohydride and citrate and then mixing the solution with the carrier. Alternatively, the nanoreactor solution may be formed by synthesizing nanoparticles with the first metal precursor in situ by adding the carrier.

In Situ Production of Nanoreactor Solution Using a First Metal Precursor and Carrier Reagents Hydrogen tetrachloroaurate (III) trihydrate ($HAuCl_4 \cdot 3H_2O$), silver nitrate ($AgNO_3$), and gelatin were purchased from Acros Organics. All chemicals were used as received without any purification, and all aqueous solutions were prepared in deionized Millipore water (resistivity>18 MΩ·cm).

Methods and Results

A nanoreactor was synthesized using silver precursor within gelatin matrix (AgNO$_3$ 1 mM, gelatin 0.01-0.02 g/mL). To initiate synthesis of gold nanoparticles (AuNPs), a solution comprising 0.5-2 mM hydrogen tetrachloroaurate (HAuCl$_4$) was added to the prepared silver gelatin nanoreactor. The hydrogen tetrachloroaurate (HAuCl$_4$) solution serves as a "switch" to turn on the AuNP nanoreactor and thus user initiated mixing of HAuCl$_4$ starts the product time-temperature history tracking clock.

Figure 20:
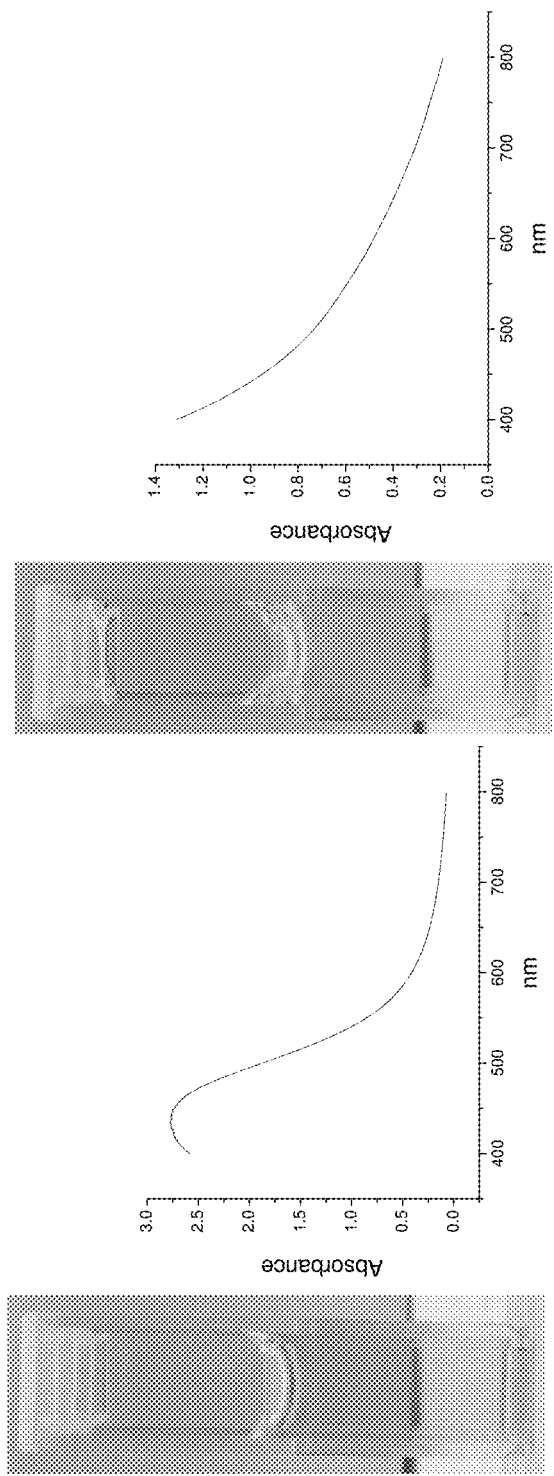
FIG. 20 shows photographs of a silver-gelatin nanoreactor and corresponding UV-visible spectrum before (left) and after (right) $HAuCl_4$ addition.
Figure 21:
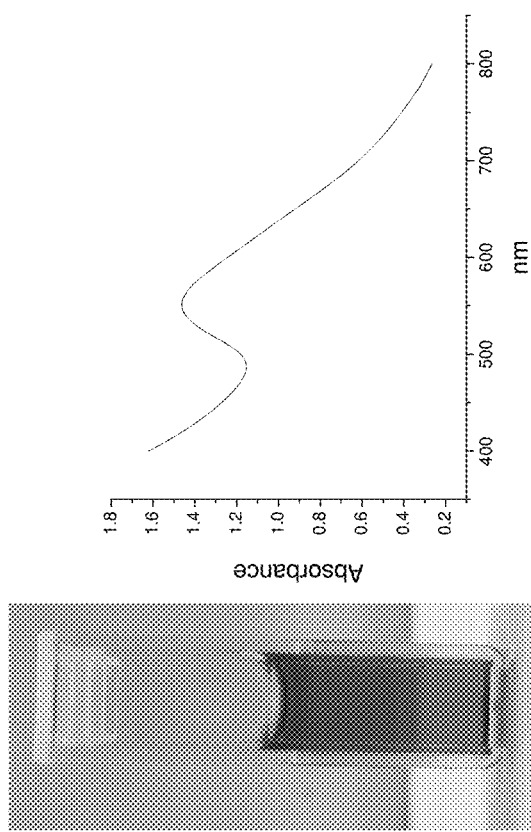
FIG. 21 shows a photograph of the gold-silver-gelatin nonreactor and corresponding UV-vis spectrum 6 hours after $HAuCl_4$ addition at room temperature.

Prior to mixing HAuCl$_4$, the nanoreactor stays yellow (FIG. 20, left). The color may change depending on the time-temperature history of the storage conditions. However, as soon as HAuCl$_4$ is added, the color disappears and the solution is blank (FIG. 20, right) and ready for further time and temperature "tracking." Thereafter, the color change, which changes with time and temperature, can be monitored. FIG. 21 shows the gold-silver-gelatin nanoreactor 6 hours after gold precursor addition and incubation at room temperature.

Figure 22:
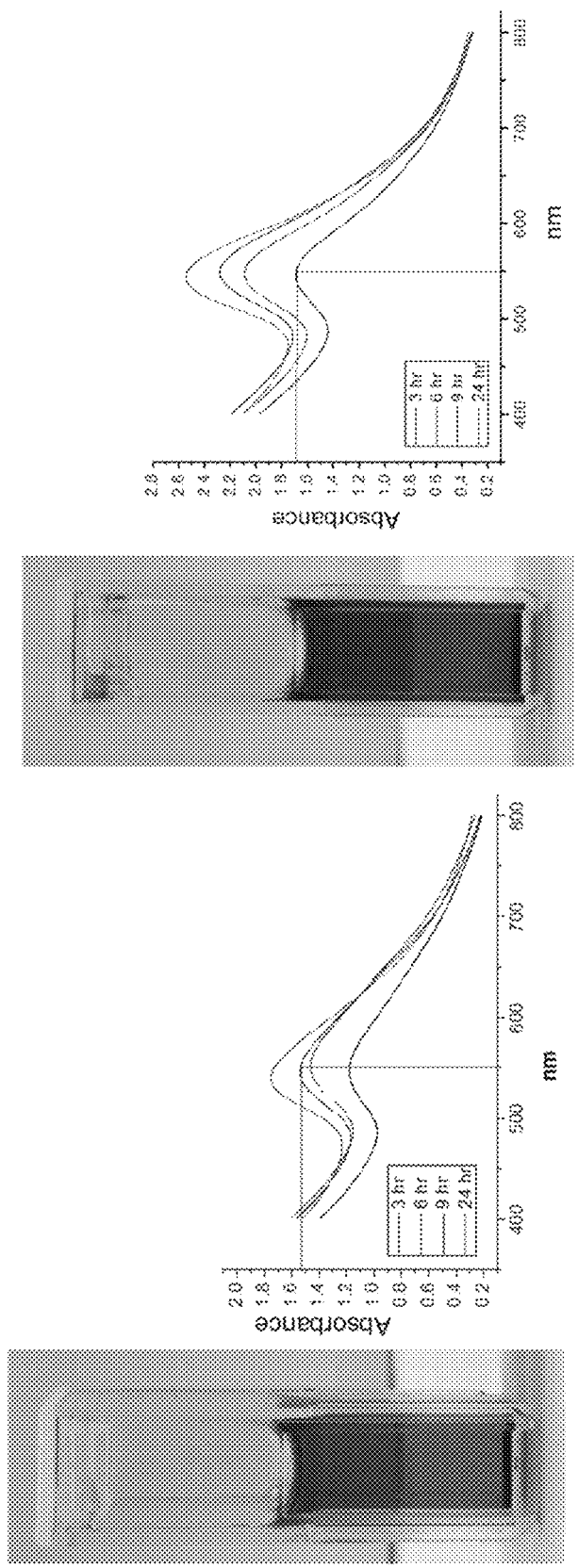
FIG. 22 shows photographs of gold-silver-gelatin nanoreactors with different compositions. The composition on the left is 0.5 mM gold precursor, 1 mM silver precursor, and 0.01 g/ml gelatin. The composition on the right is 1 mM gold precursor: 1 mM silver precursor, and 0.02 g/ml gelatin. Each composition was stored at room temperature for various time periods. The reaction in the nanoreactor on left occurs slower (reaches ~1.6 Abs at 550 nm after 9 h) than that on right (reaches ~1.6 Abs at 550 nm after 3 h).
Figure 23:
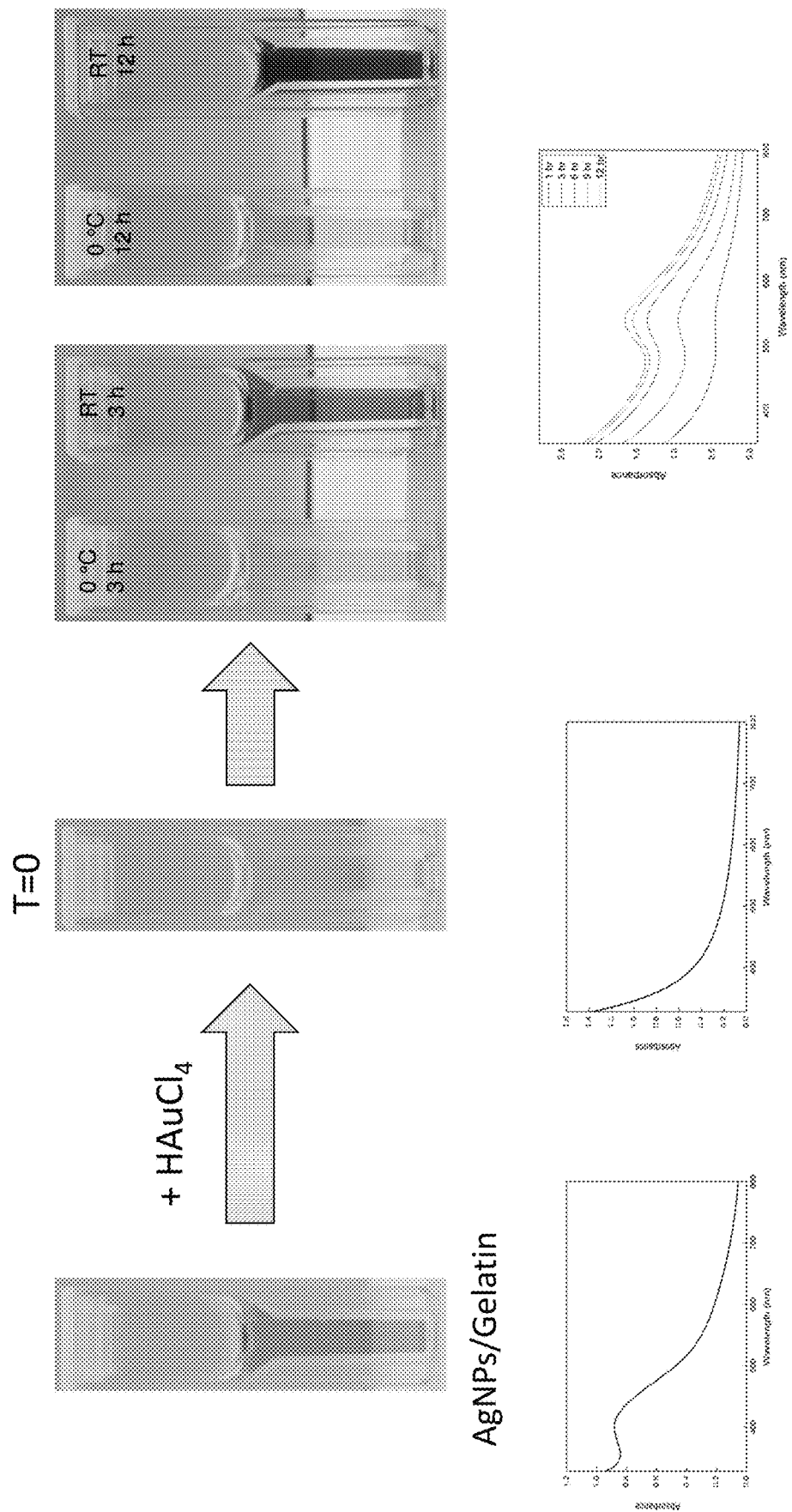
FIG. 23 shows a nanoreactor including 0.01 $g·mL^{-1}$ of gelatin and 1 mM of AgNO3, which was heated at 90° C. for 12 h (leftmost photograph and UV spectra). At T=0, gold precursor was added to the nanoreactor and the nanoreactor was placed at 0° C. or RT for 3 hours or 12 hours.

FIG. 22 illustrates the tunability of gold-silver-gelatin nanoreactors. For example, if a target threshold is set to 1.6 Abs units and 550 nm (intensity and color), the first sample (FIG. 22, left) took more than 9 hours to achieve that threshold, whereas, the second sample (FIG. 22, right) took 3 hours. The incubation temperature was at room temperature for 24 hours. The composition on the left is 0.5 mM gold precursor, 1 mM silver precursor, and 0.01 g/mL gelatin. The composition on the right is 1 mM gold precursor, 1 mM silver precursor, and 0.02 g/mL gelatin. We also show that heating time is also an adjustable parameter (FIG. 23).

Figure 24A:
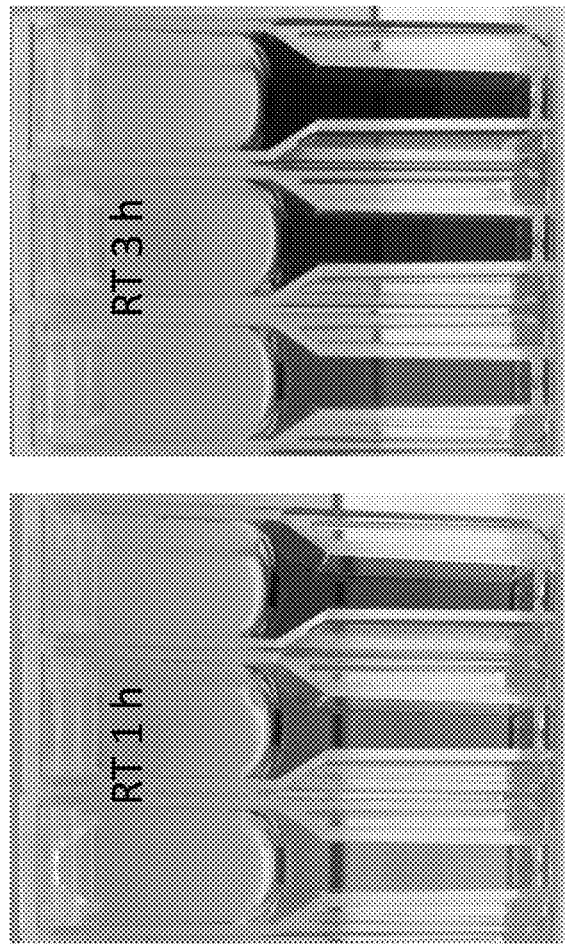
FIG. 24A shows 0.01 $g·mL^{-1}$ of gelatin plus 1 mM of $AgNO_3$, heated at 90° C. for 12 h, followed by 0.5, 1, and 1.5 mM of gold precursor addition (form left to right), after RT exposure for 1 h (left) and RT 3 h (right).
Figure 24B:
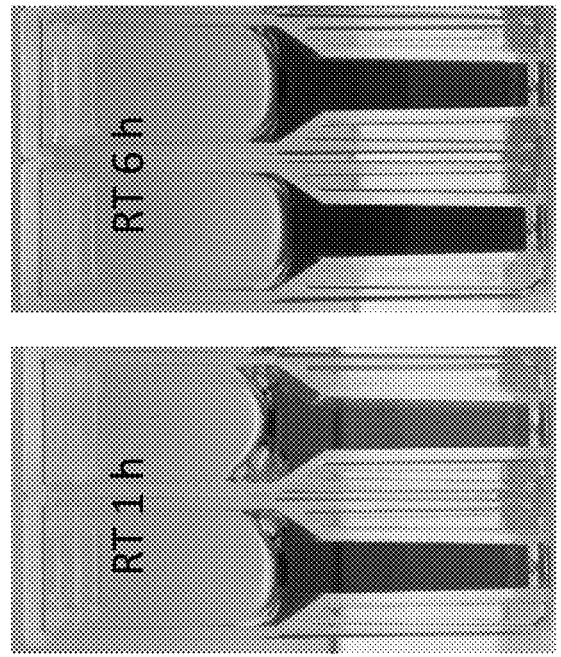
FIG. 24B shows systems with silver nanoparticles and different concentrations of gelatin (0.01 and 0.02 $g·mL^{-1}$) with 1.5 mM of gold precursor addition, after RT exposure for 1 h and RT 6 h.
Figure 24C:
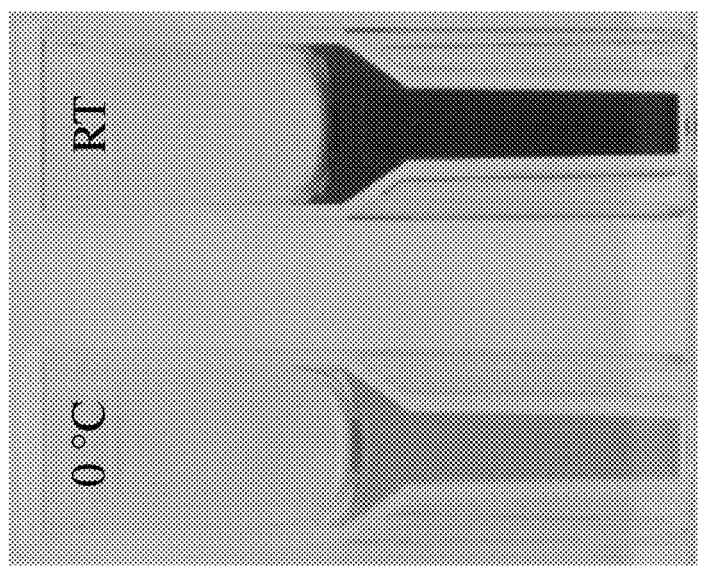
FIG. 24C shows 0.01 $g·mL^{-1}$ of gelatin plus 1 mM of $AgNO_3$, heated at 90° C. for 12 h, followed by 0.25 mM of gold precursor addition, then placed at 0° C. and RT for 14 days.

We also show that a multi-stage (starter switch) nanoreactor can be tuned easily by simply adjusting the amount of HAuCl$_4$ added (FIGS. 24A-24C). We prepared three nanoreactors initially comprised of 0.02 g·mL$^{-1}$ of gelatin plus 1 mM AgNO$_3$ and then added 0.5 mM, 1 mM and 1.5 mM of HAuCl$_4$ to each nanoreactor then placed the samples at RT for 1 hour. As shown in FIGS. 24A and 24B, the results demonstrate that the nanoreactors exhibited significantly different colors depending on the amount of HAuCl$_4$ added.

A multi-stage (starter switch) nanoreactor can also be easily tunable for different applications (FIG. 25). We prepared nanoreactors initially comprised of 0.01 g·mL$^{-1}$ of gelatin plus 1 mM AgNO$_3$ (FIG. 25A) and then added 0.25 mM, 0.5 mM, 1 mM or 1.5 mM of HAuCl$_4$ to each nanoreactor, which was placed in a refrigerator for 3 days. We also prepared nanoreactors initially comprised of 0.02 g·mL$^{-1}$ of gelatin plus 1 mM AgNO$_3$ and then added 0.5 mM, 1 mM and 1.5 mM of HAuCl$_4$ to each nanoreactor, which was placed in a refrigerator for 3 days. As shown in FIG. 25, the colors of the multi-stage (starter switch) nanoreactor varied significantly depending on the initial amount of gelatin.

A multi-stage (starter switch) nanoreactor may also be based on alginic acid (FIG. 26). We prepared an initial nanoreactor comprising 0.01 g·mL$^{-1}$ of alginic acid plus 1 mM AgNO$_3$ and heated it at 90° C. for 12 hours. At T=0, 0.5 mM of HAuCl$_4$ was added to the nanoreactor, which then was stored for 9 hours at either 0° C. or room temperature. As shown in FIG. 26, a multi-stage (starter switch) nanoreactor based on alginic acid also exhibits significantly different color changes depending on the storage temperature.
Preparation of Nanoreactor Solution Using a Reducing Agent Prior to Addition of Carrier This example demonstrates that a nanoreactor solution may be formed by synthesizing nanoparticles with the first metal precursor using any suitable reducing reagent and then mixing the solution with the carrier.

Figures 30A, 30B:
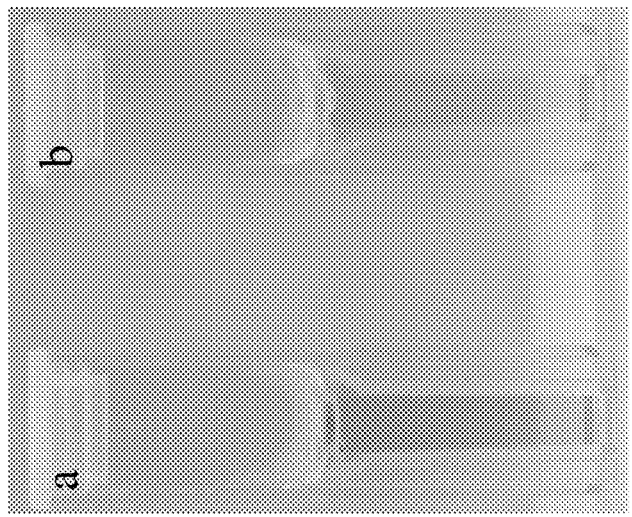
FIG. 30A shows 1 mL of silver nanoparticle/gelatin mixture.
FIG. 30B shows the nanoreactor after adding 100 µl of 10 mM $HAuCl_4$ to the nanoreactor in FIG. 30A. Silver nanoparticles were prepared by the following method. 10 mL of 1.0 mM silver nitrate was added dropwise to 30 mL of 2.0 mM ice-cold sodium borohydride solution. The mixture was stirred vigorously on a magnetic stir plate. Then 20 mL of as-prepared AgNPs were mixed with 50 mL 0.005 g/mL of gelatin solution to make the silver nanoparticle/gelatin mixture. See, e.g., Mulfinger L., *J. Chem. Educ.*, 2007, 84 (2), p 322.
Figure 31A:
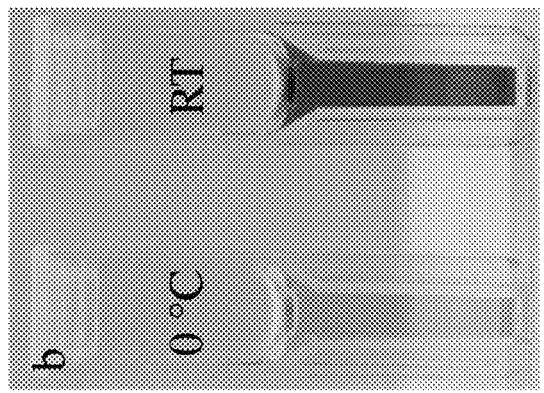
FIGS. 31A and 31C show a 1 mL of silver nanoparticle/gelatin mixture plus 50 µl of 10 mM $HAuCl_4$.
Figure 31B:
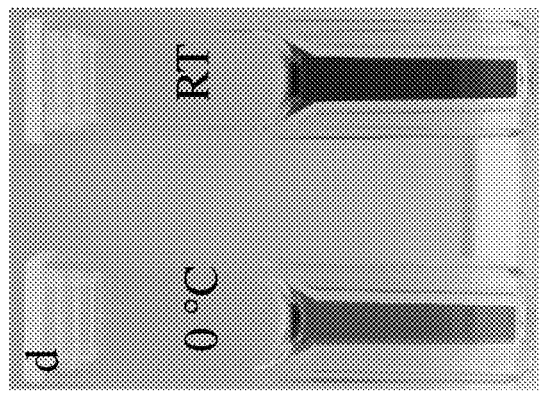
FIGS. 31B and 31D show a 1 mL of silver nanoparticle/gelatin mixture plus 50 µl of 10 mM $HAuCl_4$.
Figure 31C:
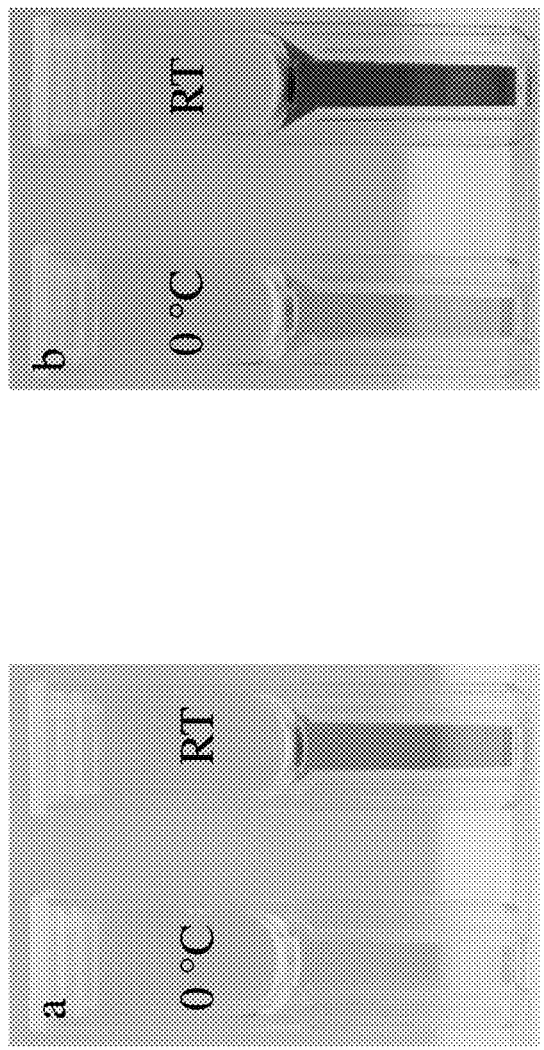
Figure 31D:
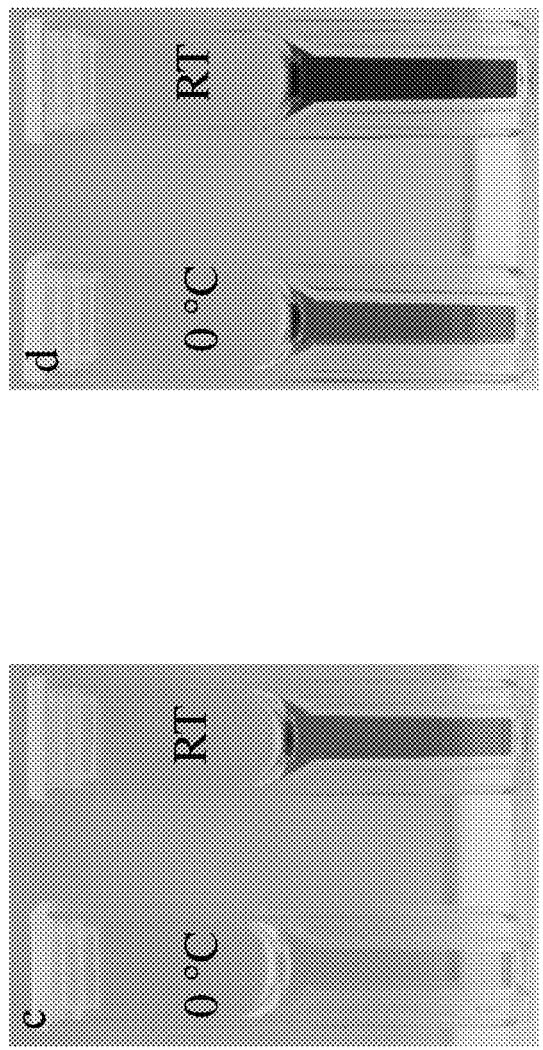

Silver nanoparticles were prepared by adding 10 mL of 1.0 mM silver nitrate dropwise to 30 mL of 2.0 mM ice-cold sodium borohydride solution. The mixture was stirred vigorously on a magnetic stir plate. The 20 mL of as-prepared AgNPs was then mixed with 50 mL 0.005 g/mL of gelatin solution to make the silver nanoparticle/gelatin mixture. See, e.g., Mulfinger L., *J. Chem. Educ.*, 2007, 84 (2), p 322; (FIG. 30A). As shown in FIG. 30B, the nanoreactor became clearer after adding 100 µl of 10 mM HAuCl$_4$ to the nanoreactor FIGS. 31A and 31C show a 1 mL of silver nanoparticle/gelatin mixture plus 50 µl of 10 mM HAuCl$_4$. FIGS. 31B and 31D show a 1 mL of silver nanoparticle/gelatin mixture plus 50 µl of 10 mM HAuCl$_4$. FIGS. 31A and 31B show 1 hr at 0° C. and RT. FIGS. 31C and 31D show 9 hr at 0° C. and RT (All these silver nanoparticles were synthesized alone and then added into gelatin.). As the storage temperature increased, along with the storage duration, the color becomes deeper. It is also tunable by changing the amount of gold precursor, gelatin concentration, amount of silver nanoparticles.

Example 5—Nanoreactors Comprising Two Biopolymers

Figure 27:
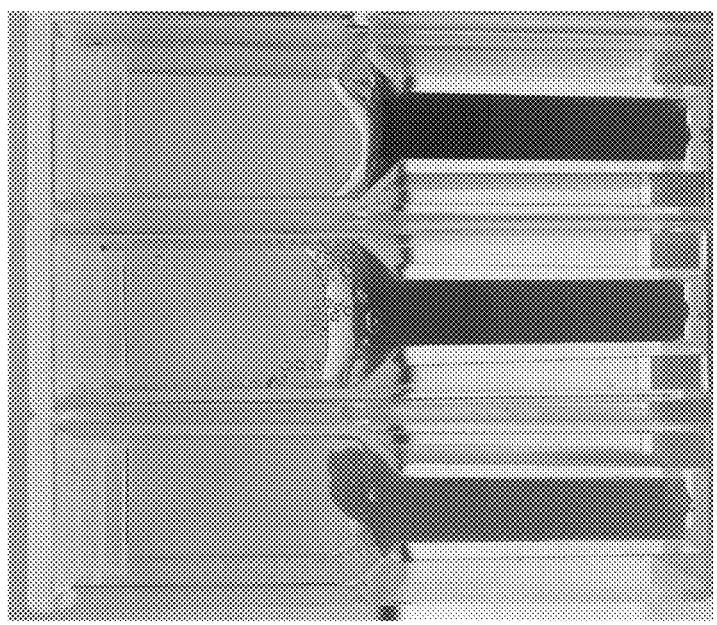
FIG. 27 shows a nanoreactor based on two biopolymers—alginic acid and gelatin. An initial nanoreactor comprising 0.005 $g·mL^{-1}$ alginic acid and 0.005 $g·mL^{-1}$ gelatin was prepared. 1 mM of $HAuCl_4$ was added to the initial nanoreactor and the nanoreactor was heated at 90° C. for 15 min. The nanoreactor was then placed at different temperatures (−20° C. (left), 0° C. (middle), room temperature (RT) (right)) for 3 days.

We also demonstrate that a nanoreactor may be based on two biopolymers such as alginic acid and gelatin (FIG. 27). We prepared an initial nanoreactor comprising 0.005 g·mL$^{-1}$ alginic acid and 0.005 g·mL$^{-1}$ gelatin and then added 1 mM of HAuCl$_4$ to the initial nanoreactor and then heated the nanoreactor at 90° C. for 15 min. The nanoreactor was then placed at different temperatures (−20° C. (left), 0° C. (middle), room temperature (RT) (right)) for 3 days. As shown in FIG. 27, the color of the nanoreactor differed depending on the storage temperature.

We claim:

1. A nanoreactor comprising a metal precursor and a carrier, wherein the carrier comprises a polymer capable of acting as a reducing agent and capable of stabilizing nanoparticles formed from the metal precursor at a temperature below 0° C.

2. The nanoreactor of claim 1, wherein said metal precursor is a gold precursor.

3. The nanoreactor of claim 1, wherein the carrier comprises chitosan.

4. The nanoreactor of claim 3, wherein a concentration of the metal precursor is between 0.2 mM and 3 mM and a concentration of the chitosan is between 0.0006 g/mL and 0.0004 g/mL.

5. A nanoreactor comprising a metal precursor and a carrier comprising alginic acid and a divalent ion, wherein the carrier comprises a polymer capable of acting as a reducing agent and capable of stabilizing nanoparticles formed from the metal precursor in a gel.

6. The nanoreactor of claim 5, wherein the a divalent ion is Ca$^{2+}$.

7. The nanoreactor of claim 5, wherein nanoreactor is gelled.

8. The nanoreactor of claim 5, wherein a concentration of the metal precursor is between 0.2 mM and 3 mM and a concentration of the alginic acid is between 0.001 g/mL and 0.1 g/mL.

9. Packaging for the detection of exposure of a perishable good to an undesired temperature, the packaging comprising a nanoreactor suitable for inclusion with the perishable good, wherein the nanoreactor comprises the nanoreactor of claim 1.

10. A method of determining a thermal history of a nanoreactor comprising detecting at least one characteristic of said nanoreactor and based on said characteristic determining whether said nanoreactor was exposed to an undesired temperature for a time period, wherein said nanoreactor is the nanoreactor of claim 1.

11. A method of detecting exposure of a perishable good to an undesired temperature comprising detecting at least one characteristic of a nanoreactor packaged in association with the perishable good and based on said characteristic determining whether said nanoreactor was exposed to an undesired temperature for a time period, wherein said nanoreactor is the nanoreactor of claim 1.

12. The method of claim 11, wherein the undesired temperature is below 0° C.

13. The method of claim 11, wherein the carrier comprises chitosan.

14. A method of determining a thermal history of a nanoreactor comprising detecting at least one characteristic of said nanoreactor and based on said characteristic determining whether said nanoreactor was exposed to an undesired temperature for a time period, wherein said nanoreactor is the nanoreactor of claim 5.

15. A method of detecting exposure of a perishable good to an undesired temperature comprising detecting at least one characteristic of a nanoreactor packaged in association with the perishable good and based on said characteristic determining whether said nanoreactor was exposed to an undesired temperature for a time period, wherein said nanoreactor is the nanoreactor of claim 5.

16. The method of claim 15, wherein the nanoreactor is gelled.

17. The method of claim 15, wherein the divalent ion is $Ca^{2+}$.

18. Packaging for the detection of exposure of a perishable good to an undesired temperature, the packaging comprising a nanoreactor suitable for inclusion with the perishable good, wherein the nanoreactor comprises the nanoreactor of claim 5.

* * * * *